United States Patent
Jain et al.

(10) Patent No.: US 10,756,957 B2
(45) Date of Patent: Aug. 25, 2020

(54) CONTEXT BASED NOTIFICATIONS IN A NETWORKED ENVIRONMENT

(71) Applicant: Vignet Incorporated, Fairfax, VA (US)

(72) Inventors: Praduman Jain, Fairfax, VA (US); Josh Schilling, Newberg, OR (US)

(73) Assignee: Vignet Incorporated, Fairfax, VA (US)

( * ) Notice: Subject to any disclaimer, the term of this patent is extended or adjusted under 35 U.S.C. 154(b) by 50 days.

(21) Appl. No.: 15/804,201

(22) Filed: Nov. 6, 2017

(65) Prior Publication Data

US 2019/0140892 A1    May 9, 2019

(51) Int. Cl.

| | |
|---|---|
| *H04L 29/08* | (2006.01) |
| *H04L 12/24* | (2006.01) |
| *H04L 12/26* | (2006.01) |
| *H04L 12/18* | (2006.01) |
| *G16H 10/60* | (2018.01) |
| *H04L 12/58* | (2006.01) |
| *G16H 15/00* | (2018.01) |
| *G16H 50/70* | (2018.01) |
| *G16H 50/30* | (2018.01) |

(52) U.S. Cl.
CPC .......... *H04L 41/0686* (2013.01); *H04L 41/16* (2013.01); *H04L 67/327* (2013.01); *G16H 10/60* (2018.01); *G16H 15/00* (2018.01); *G16H 50/30* (2018.01); *G16H 50/70* (2018.01); *H04L 12/1895* (2013.01); *H04L 43/0811* (2013.01); *H04L 51/26* (2013.01); *H04L 67/12* (2013.01); *H04L 67/22* (2013.01); *H04L 67/24* (2013.01)

(58) Field of Classification Search
CPC ..... H04L 67/12; H04W 4/029; G06F 19/3418
See application file for complete search history.

(56) References Cited

U.S. PATENT DOCUMENTS

| | | |
|---|---|---|
| 8,612,263 B1 | 12/2013 | Atkinson et al. |
| 9,245,262 B1 | 1/2016 | Avatara |
| 9,361,011 B1 | 6/2016 | Burns |

(Continued)

OTHER PUBLICATIONS

Final Office Action in U.S. Appl. No. 15/382,126, dated Aug. 30, 2017, 22 pages.

(Continued)

*Primary Examiner* — Tom Y Chang
(74) *Attorney, Agent, or Firm* — Fish & Richardson P.C.

(57) ABSTRACT

The systems and methods of the invention provide a notification system that analyzes the state of the user to deliver notifications when the user is anticipated to be both cognitively receptive AND able to act upon external stimuli. In accord with at least one aspect, the system assesses the context (of a user) by interpreting the user and surroundings in order to reach a general state of the user. In a technically efficient manner—utilizing different levels of processing in conjunction with leveraging previously performed processing through queuing results of such processing—the system provides the ability to reduce scenarios in which missed or inappropriate notifications occur. The systems and methods of the invention perform processing, in a technically efficient manner, to assess data input from sensors (in the real-world environment in which a user exists) and responsively generate appropriate notifications or other communications that are output to a user or a person associated with the user.

15 Claims, 26 Drawing Sheets

(56) References Cited

U.S. PATENT DOCUMENTS

| | | |
|---|---|---|
| 9,426,433 B1 | 8/2016 | Mazzarella |
| 9,461,972 B1 | 10/2016 | Mehta |
| 10,069,934 B2 | 9/2018 | Jain et al. |
| 2001/0019338 A1 | 9/2001 | Roth |
| 2002/0022973 A1 | 2/2002 | Sun |
| 2005/0086587 A1 | 4/2005 | Balz |
| 2005/0186550 A1 | 8/2005 | Gillani |
| 2006/0107219 A1 | 5/2006 | Ahya |
| 2008/0005679 A1 | 1/2008 | Rimas-Ribikauskas |
| 2008/0127040 A1 | 5/2008 | Barcellona |
| 2009/0024944 A1 | 1/2009 | Louch |
| 2009/0043689 A1 | 2/2009 | Yang |
| 2009/0163182 A1 | 6/2009 | Gatti |
| 2009/0172002 A1 | 7/2009 | Bathiche |
| 2010/0041378 A1 | 2/2010 | Aceves |
| 2010/0295676 A1 | 11/2010 | Khachaturov et al. |
| 2011/0200979 A1 | 8/2011 | Benson |
| 2012/0102050 A1 | 4/2012 | Button |
| 2012/0170724 A1* | 7/2012 | Yoakum ................. H04L 51/22 379/88.22 |
| 2012/0272156 A1 | 10/2012 | Kerger |
| 2013/0110565 A1 | 5/2013 | Means |
| 2013/0166494 A1 | 6/2013 | Davis |
| 2013/0238686 A1 | 9/2013 | O'Donoghue |
| 2013/0326375 A1 | 12/2013 | Barak et al. |
| 2014/0088995 A1 | 3/2014 | Damani |
| 2014/0100883 A1 | 4/2014 | Hamilton |
| 2014/0156823 A1 | 6/2014 | Liu |
| 2014/0181715 A1 | 6/2014 | Axelrod |
| 2014/0240122 A1 | 8/2014 | Roberts |
| 2014/0273913 A1 | 9/2014 | Michel |
| 2015/0088955 A1 | 3/2015 | Hendrick et al. |
| 2015/0099458 A1* | 4/2015 | Weisner ................. H04W 84/22 455/15 |
| 2015/0135160 A1 | 5/2015 | Gauvin |
| 2015/0148061 A1 | 5/2015 | Koukoumidis |
| 2016/0058287 A1 | 3/2016 | Dyell |
| 2016/0220177 A1* | 8/2016 | Proud ................. A61B 5/4809 |
| 2016/0300570 A1 | 10/2016 | Gustafson et al. |
| 2018/0049675 A1* | 2/2018 | Kerber ................. A61B 5/0205 |
| 2018/0176331 A1 | 6/2018 | Jain et al. |
| 2019/0068753 A1 | 2/2019 | Jain et al. |

OTHER PUBLICATIONS

Final Office Action in U.S. Appl. No. 16/120,083, dated Mar. 2, 2020, 26 pages.

KhanAcademy.org, [online] "Khan Academy," Available on or before Nov. 2, 2012, via Internet Archive: Wayback Machine URL <http://web.archive.org/web/20111202083549/http://www.khanacademy.org/> retrieved Mar. 11, 2020, 20 pages.

Non-Final Office Action in U.S. Appl. No. 15/382,126, dated Mar. 17, 2017, 17 pages.

Non-Final Office Action in U.S. Appl. No. 16/120,083, dated Sep. 26, 2019, 22 pages.

* cited by examiner

Processing relates to how the user profile is "tuned" in an ongoing manner.

Fig. 6

320 System monitors communication channels to engage with existing user over network to modify user profile (e.g. based on input survey information) (from Fig. 3)

321 System periodically reaches out to user(s) to invite feedback regarding disposition of such user(s).

323 If feedback (from user) is inconsistent with current handling of user, the system makes adjustments to address a user's changing needs and/or how a user is observed to react to the system.

322 System determines whether the feedback received is consistent with the current handling of the user, e.g. what "program" the user is currently enrolled in as represented by the user profile.

324 Changes applied to a user (based on feedback from that user and others) may then be applied to other similarly situated users, i.e. changes in the profile of a user may be extrapolated to other similarly situated users.

Fig. 10

- Comparator functions include more than just limited threshold detectors. Also, trending, patterns, including nonlinear dynamics and chaos theory like Correlation Dimension (CD) among others.

- Comparator processing requires metadata tags for follow-up reviews, i.e. subsequent processing of data to assess correlation of data, for example.

- Essentially the comparative processing is looking to see if a system event should be queued based on some early criteria for selection. For example, a too high, too low, spike, large difference, etc… style of scenario is detected by the system.
- Such processing assists in reducing battery consumption if processed on the phone, or bandwidth to the network, etc.
- Processing of invention allows processor to operate more efficiently.

Fig. 11

Tagging data serves to, for example:

- preserve knowledge of system regarding data;

- correlate such data with other data (at later time) so as to identify/understand patterns or trends;

- understand duplicate data or stagnate data; and

- in general assist in storing and archiving data for current and/or later use.

Fig. 13

Data record maps the following, 1. type of comparison (limit, trend, math function like chaos theory, multiple, etc...), 2. what are the changing conditions that can spur a suggested SE. Delta of change from previous condition. E.g. Last heart rate was 90 bpm, but has dropped to 60 bpm, this sudden decrease may mean that stress has been reduced.

The "conditions" that can spur a "suggested SE" by the system may change over time, in particular for a particular user and is dependent on the context of the user.

- For example, the system may learn that a particular user is an athlete and adjust heart bpm thresholds based on such learned data.

Computer table 1400

Fig. 14

1401 record

| Record Identifier | Sensor data (Observed) | Pre-qualifier Type(s) | Pre-qualifier |
|---|---|---|---|
| R-10102 | Heart Rate | High Limit, Low Limit, Delta Shift, Other Operands | (220-Age*80%), 30BPM, -10BPM, Downward |

- This data table 1400 with record 1401 is provided as an example in the context of the processing of Fig. 12.

- For other comparator functions, system may utilize various additional tables with metadata references between tables, for example.

1400'

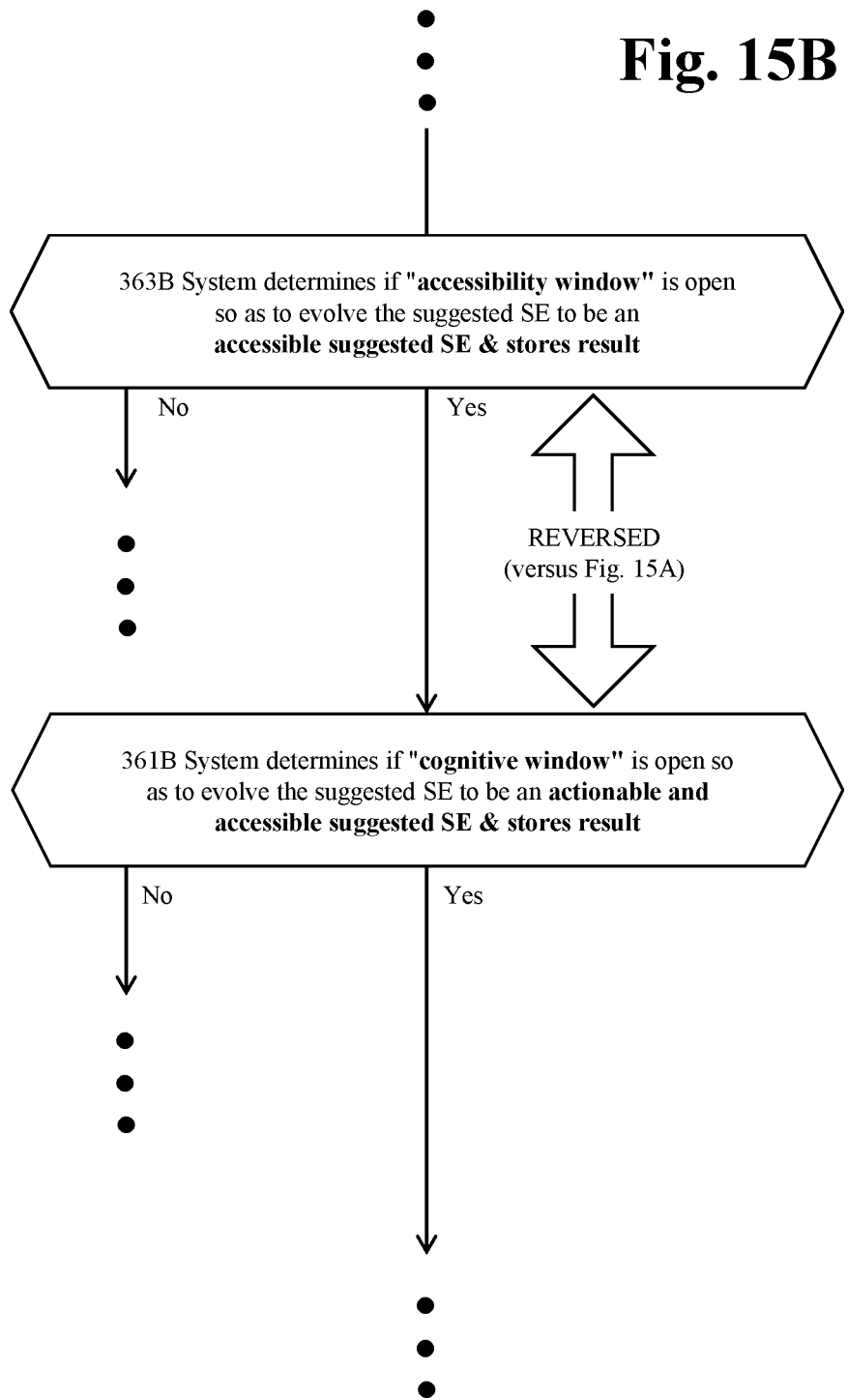

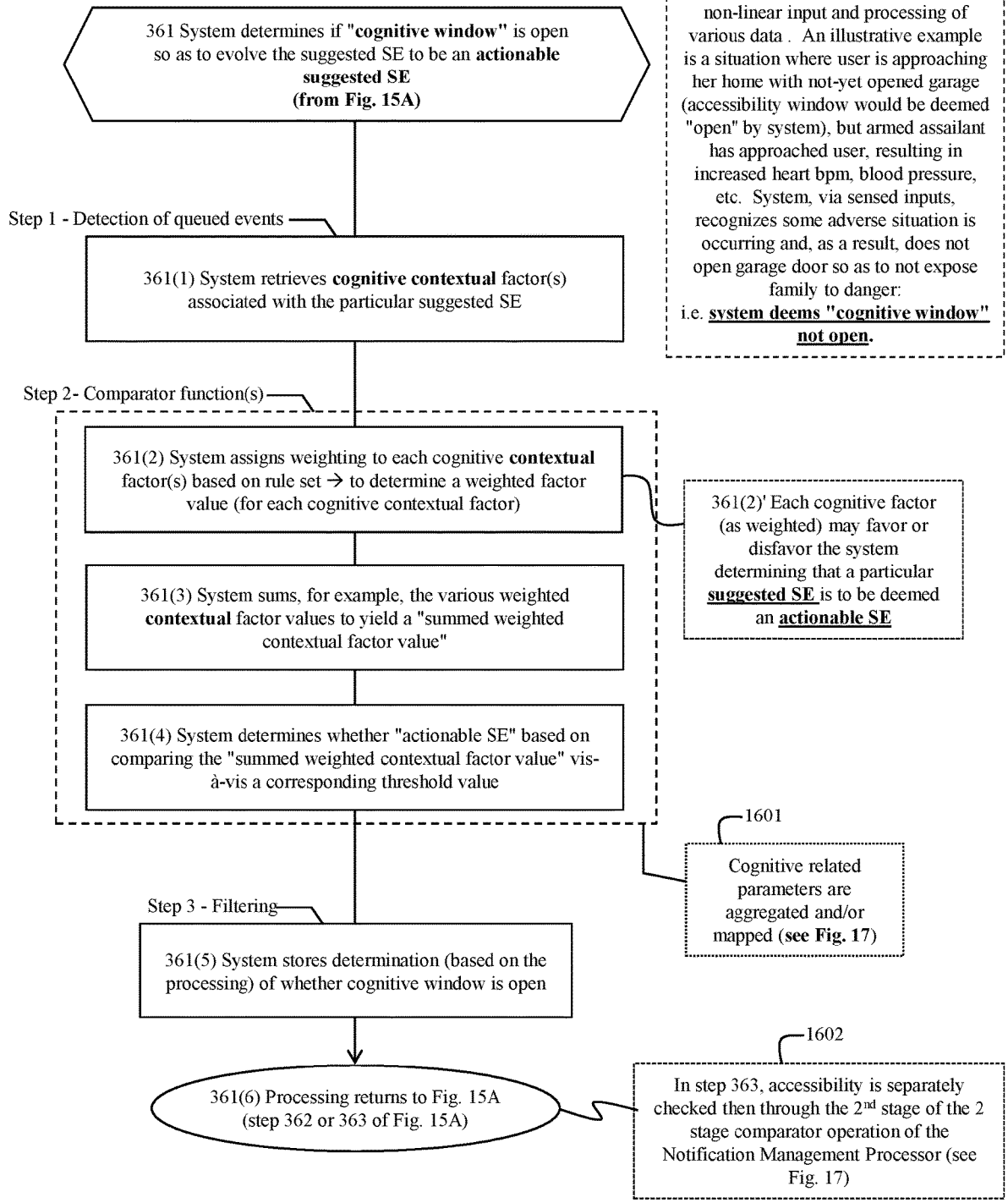

Fig. 17

1701 — The determination of whether a "cognitive window" is "open" = a determination by the system of whether predetermined criteria is satisfied. e.g. a predetermined pattern is satisfied, for example.

In this processing, cognitive parameters are mapped to determine if the user is cognitively aware and can possibly accept an upcoming notification or pending notification, etc.

Example.

1. the user's heart rate is elevated would indicate stress through a lookup;

2. The user's calendar is full of side-by-side meetings would indicate her activity is busy;

3. The user is currently running, so she is also performing a task;

So illustrative processing may include:

Trigger the notification if the following conditions are met.
Heart Rate = Moderate (not sleeping)
AND
Busy = Moderate to Low (not too busy)
AND
Not currently performing a task (i.e. Running)
AND
There isn't a major storm (i.e. Hurricane)
AND
EEG shows individual is not depressed currently (mild improvement would be ok based on trending and situations)
= User should accept notification presented
Otherwise, may need to forward notification to someone else in the system such as a caregiver if too much time elapses or if the priority is high enough due to number of high priority queued triggers.

1702 — This processing maps "cognitive parameters" (i.e. input data that relates to the "cognitive" situation of user) to determine if the cognitive parameters reflect a scenario in which the user/caregiver can accept a notification.

• Such mapping may include determining if the observed inputs correspond to particular criteria a pattern, satisfaction of a Boolean requirement, satisfaction of a particular weighting or sum of weights amongst particular inputs; and/or satisfaction of particular threshold value or values, for example.

Fig. 19

Mapping

Processing maps "accessibility parameters" (i.e. input data that relates to the "accessibility" situation of user) to determine if the accessibility parameters reflect a scenario in which the user/caregiver can accept a notification.

The accessibility parameters may be data input from sensors or other type of data.

Such mapping may include, for example, determining if the observed inputs correspond to predetermined criteria:

- satisfaction of a particular pattern,
- satisfaction of a Boolean requirement,
- satisfaction of a particular weighting,
- satisfaction of a sum of weights amongst all inputs,
- satisfaction of a sum of weights amongst particular inputs, and/or
- satisfaction of particular threshold value or values, for example.

1900

CONTEXT BASED NOTIFICATIONS IN A NETWORKED ENVIRONMENT

FIELD OF THE INVENTION

The systems and methods described herein relate to the processing of input digital data in a networked environment of computer processing devices, amongst a networked community of users, in conjunction with generating one or more related electronic communications.

BACKGROUND

In the present technological environment, various services, user device applications and other platforms provide information and notifications to users based on observed events and/or in some predetermined scheduled manner, for example.

Current notifications systems are designed to send notifications to users uncertain if the user will see or act upon the notification. Therefore, notifications are often sent more than once. Such systems may have fallback notification options if the first notification attempt was unsuccessful. However, this leads to even more notifications being transmitted, inefficient use of the devices, inefficiency of the communication channels, and inefficiency of the network. The current inefficient systems not only clog networks with multiple and redundant notifications, they also clog the user's device with redundant notifications, consume excessive power of the user's device and the network, and consume bandwidth. These inefficiencies cost the consumer and provider.

Therefore, technical improvements and solutions are needed to overcome this technical problem while accommodating the evolving needs of users. The systems and methods of the present invention provide such improvements.

SUMMARY

The systems and methods of the invention provide a notification system that analyzes the state of the user to deliver notifications when the user is anticipated to be both cognitively receptive AND able to act upon external stimuli. In accord with at least one aspect, the system assesses the physiological context (of a user) both inward and outward by interpreting the user and surroundings in order to reach a general state of the user. In a technically efficient manner— utilizing different levels of processing in conjunction with leveraging previously performed processing through queuing results of such processing—the system provides the ability to reduce scenarios in which missed or inappropriate notifications (due to cancellation by user, inability to react, and avoidance due over stimuli, for example) occur. In accord with aspects of the invention, systems and methods of the invention perform processing, in a technically efficient manner, to assess data input from sensors (in the real-world environment in which a user exists) and responsively generate appropriate notifications or other communications that are output to a user or a person associated with the user.

In accord with at least one aspect, from a high-level, the system in the background evaluates one or more signals, i.e. inputs for example, driving a suggested notification before responding to such input. The signal is evaluated by reviewing its criteria for notifications along with the physiology of the user. The system makes the determination both whether the signal triggering the request is meaningful, and if the user, at that moment in time, should or could react to a notification. The system can otherwise, delay, dismiss or transfer the notification between users of the system and/or persons associated with users of the system, in accordance with at least one aspect of the invention.

Because evaluating the anticipated reaction and reception of the user is subjective, the system must know more about the individual and her surroundings in order to provide a meaningful action on behalf of the user. This requires the assessment of physiological data as a genetic makeup for the internal processing—including the processing required to determine whether the message is appropriate and deliverable.

In the systems and methods of the invention, assessment is carried out by collecting information either directly by the server or servers or through a backend server counterpart that can synchronize with the application. Information that is collected may occur through several interfaces that enable communication to environmental sensors, health sensors, activities and tasks, and economy inputs, for example. Each of these interfaces, devices and sensors help convey, to the system, data regarding what the user is currently doing, what she might be feeling, where she might be, and whether it's a good time to ask the particular user to perform a particular task, for example.

Once these many data points are interpreted such data points are matched to a given scenario for the user that can change how the notification message appears, what sound it plays, and what device or system it is delivered to for best responsiveness.

The present invention provides a system of networked apparatuses that provide cognitive-like processing based on an aggregation of input data, the processing performed over a network to provide a communication interface amongst the networked apparatuses, each of the apparatuses in the form of a tangibly embodied computer processor, each computer processor including instructions on a non-transitory computer medium disposed in a corresponding database, the system comprising: the network over which the networked apparatuses communicate; a plurality of the networked apparatuses respectively being a data providing (DP) processor, each DP processor provided to input user data regarding a user; a CAND (Context Aware Notification Delivery) server, the CAND server including: a communication portion that interfaces with each of the DP computer processors; a database; and a CAND computer processor, the CAND computer processor performing processing for first window criteria including: interfacing with a first DP processor over the network to input first input data; interfacing with a second DP processor over the network to input second input data; performing first processing to generate a first data aggregation based on at least the first input data and the second input data; performing a determination of whether the first data aggregation satisfies first window criteria; determining that the first data aggregation does not satisfy the first window criteria, but that the first data aggregation does satisfy criteria for a suggested event, and the CAND server, based on the determination of satisfaction of criteria for the suggested event, generating queue data based on said first data aggregation; the CAND computer processor performing processing for second window criteria including: interfacing with a third DP processor over the network to input third input data; interfacing with a fourth DP processor over the network to input fourth input data; performing second processing to generate a second data aggregation based on at least the third input data and the fourth input data; performing a determination of whether the second data aggregation satisfies second window criteria;

determining that the second data aggregation does not satisfy the second window criteria; the CAND computer processor performing further processing for the first window criteria including: interfacing with a fifth DP processor over the network to input fifth input data; performing third processing to generate a third data aggregation based on the queue data in conjunction with the fifth input data; performing a determination of whether the third data aggregation satisfies the first window criteria; determining that the third data aggregation does satisfy the first window criteria; the CAND computer processor performing further processing for the second window criteria including: interfacing with a DP processor over the network to input further input data; performing fourth processing to generate a fourth data aggregation based on at least the further data; performing a determination of whether the fourth data aggregation satisfies the second window criteria; determining that the fourth data aggregation does satisfy the second window criteria; the CAND computer processor performing further processing including: performing a determination of whether the first window criteria and the second window criteria are both satisfied; determining that the first window criteria and the second window criteria are both satisfied; and sending, based on the determination that first window criteria and second window criteria are both satisfied, a notification communication associated with the user.

The network may include further data including at least one of the third input data and the fourth input data, such that the fourth processing to generate the fourth data aggregation is performed based on (a) the further data and (b) at least one of the third input data and the fourth input data. The further data including both the third input data and the fourth input data, such that the fourth processing to generate the fourth data aggregation is performed based on (a) the further data and (b) both the third input data and the fourth input data.

One of the plurality of the DP processors may be the CAND server. The first window criteria may be the cognitive window constituted by some first criteria set, and the first criteria set is based in cognitive related attributes. The first criteria set might include at least one of a requisite threshold and a requisite summation of values. The CAND computer processor may assign a weight to at least one of the first input data, the second input data and the fifth input data. The second window criteria might be an accessibility window constituted by some second criteria set, and the second criteria set might be based in accessibility related attributes. The second criteria set might include a requisite threshold and a requisite summation of values. The CAND computer processor might assign a weight to at least one of the third input data, the fourth input data and the sixth input data. One of the DP processors might input data from a sensor associated with the user. The sensor associated with the user might be a heart rate sensor and/or a proximity sensor. The CAND computer processor might determine a communication path, to a target recipient, based on the data input from the DP sensors. The second window criteria might relate to communication data that is associated with the communication path. The target recipient could be the user, or a caregiver associated with the user. The fourth processing, regarding the second window criteria, could be performed as a result of the third processing in which the first window is determined to have been satisfied.

The present invention also provides a notification network providing improved efficiency of sending notifications to a user. The network including a plurality of devices associated with the user; an efficiency analysis processor including instructions on a non-transitory computer medium, the non-transitory computer medium constituted by one of more data storage mediums; a database of known data about the user and the plurality of devices, the database resident on the non-transitory computer medium; and a notification system that sends notification communications to the user through one or more of the plurality of devices. The plurality of devices, efficiency analysis processor, database, and notification system are in communication to form the notification network. Further, the efficiency analysis processor determines physical accessibility of the user by comparing current data from the plurality of devices in the network against known data in the database relating to the user's physical accessibility. The efficiency analysis processor also determining cognitive accessibility of the user by comparing current data from the plurality of devices in the network against known data relating to the user's cognitive abilities. Accordingly, the efficiency analysis processor generates and sends instructions, constituted by generating instruction data and sending the instruction data in a signal, to the notification system to send a notification communication to the user when the following conditions are met: (1) the efficiency analysis processor has determined the notification should be transmitted to the user; (2) the efficiency analysis processor has determined the user is physically accessible; and (3) the efficiency analysis processor has determined the user is cognitively accessible.

The plurality of devices in the network might include computing devices and sensors. The efficiency analysis processor determining physical accessibility of the user based on data associated with the user's use of one of the plurality of devices. Such device may be the user's mobile phone. The devices could include includes a first sensor in the user's home, a second sensor in the user's office, and the user's mobile phone. The plurality of devices could also include a companion computing device associated with a family member of the user or a caregiver. The sensor could be a proximity sensor. The efficiency analysis processor could determine which of the plurality of devices to transmit the notification based on power data of a device, the device being one of the plurality of devices associated with the user. The power data could be the power level of the device or the power consumption profile of the device. The efficiency analysis processor could also determine which of the plurality of devices to transmit the notification based on network efficiency data. The network efficiency data could be the cost of bandwidth along the communication path to a device associated with the user, or the communication path reliability to a device associated with the user, the device being one of the plurality of devices associated with the user. The efficiency analysis processor determining which of the plurality of devices to transmit the notification based on the reliability of the communication path and the cost of bandwidth to a device associated with the user, the device being one of the plurality of devices associated with the user. The instruction data to the notification system could include identification information on which of the plurality of devices should receive the notification. The instruction data to the notification system could include information on the identification of which communication path should be used for sending the notification. The communication path could include one or more paths or links.

The present invention could also provide a notification system, method or software for providing improved efficiency of transmitting a notification to a user. The system could be comprised of: an efficiency analysis processor including instructions on a non-transitory computer medium, the non-transitory computer medium constituted by one of more data storage mediums; a database of known data about the user and about a plurality of devices associated with the user, the database resident on the non-transitory computer medium; and a notification system that transmits notification communications to the user through one or more of the devices. The efficiency analysis processor would be in communication with the plurality of devices associated with the user, the plurality of devices. The devices could be computing devices or sensors, or a combination of many. The efficiency analysis processor could determine the physical accessibility of the user by comparing current data from the devices against known data in the database relating to the user's physical accessibility. The efficiency analysis processor could also determine the cognitive accessibility of the user by comparing current data from the devices against known data relating to the user's cognitive accessibility. Further, the system or the efficiency analysis processor can generate and send instructions, constituted by generating instruction data and sending the instruction data in a signal, to the notification system to send the notification to the user when the following conditions are met: (1) the efficiency analysis processor has determined the notification should be transmitted to the user; (2) the efficiency analysis processor has determined the user is physically accessible; and (3) the efficiency analysis processor has determined the user is cognitively accessible.

Various other features of the systems and methods of the invention are described below.

BRIEF DESCRIPTION OF THE DRAWINGS

The present invention will be better understood on reading the following detailed description of non-limiting embodiments thereof, and on examining the accompanying drawings, in which:

FIG. 6 is a diagram showing in further detail the "system monitors communication channels to engage with an existing user to modify user profile, step of FIG. 3, in accordance with at least one embodiment of the invention.

FIG. 10 is a diagram showing further details of "comparative" processing performed by the CAND system, in accordance with at least one embodiment.

FIG. 11 is a diagram showing further aspects of tagging data, in accordance with at least one embodiment of the invention.

FIG. 13 is a diagram showing aspects of data record mapping in accordance with at least one embodiment of the invention.

FIG. 14 is a diagram showing a computer table with data records in accordance with at least one embodiment of the invention.

FIG. 15B is a flowchart showing processing in reverse manner to the processing of FIG. 15A, in accordance with at least one embodiment of the invention.

FIG. 16 is a flowchart showing further details the "system determines if cognitive window is open so as to evolve the suggested system event to be an actionable suggested system event, step of FIG. 15, in accordance with at least one embodiment of the invention.

FIG. 17 is a diagram showing further details of cognitive window processing, in accordance with at least some embodiments of the invention.

FIG. 19 is a diagram showing in further detail the mapping of accessibility parameters, in accordance with at least one embodiment of the invention.

FIG. 5 provides an illustration of a high-level system architecture interface of the present invention, in accordance with at least one embodiment of the invention.

DETAILED DESCRIPTION

Hereinafter, aspects of the systems and methods of the invention will be described in accordance with various embodiments. As used herein, any term in the singular may be interpreted to be in the plural, and alternatively, any term in the plural may be interpreted to be in the singular.

It is appreciated that a feature of one embodiment of the invention as described herein may be used in conjunction with one or more other embodiments as may be desired.

Figure 1:
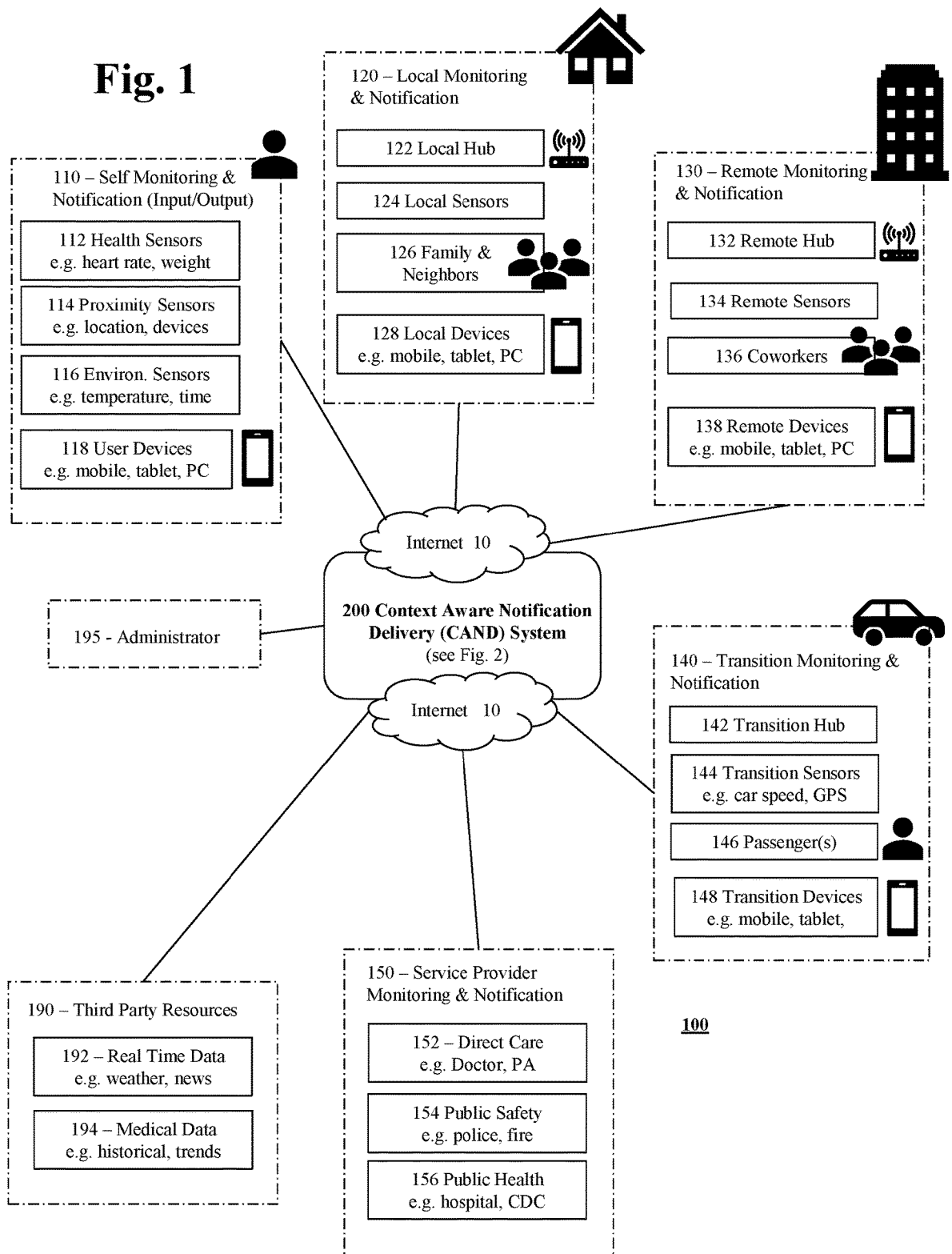
FIG. 1 is a system diagram showing a Context Aware Notification Delivery (CAND) environment, in accordance with at least one embodiment of the invention.

FIG. 1 provides an illustrative example of an exemplary embodiment of the notification system or network 100 of the present invention. The network 100 integrates or includes various environments for different settings of a user's activities. The network 100 includes various sub systems or sub-networks including Self-Monitoring & Notification 110, Local Monitoring & Notification 120, Remote Monitoring & Notification 130, Transition Monitoring & Notification 140, Service Providers Monitoring & Notification, Third Party Resources, 195, Administrator 195, and the Content Aware Notification Delivery (CAND) System 200. The sub-networks are connected to the CAND 200 via the internet 10 or other communication networks (i.e. telecom, WAN, LAN).

The Self-Monitoring & Notification 110 environment includes health sensors 112, proximity sensors 114, environmental sensors 116, and one or more user devices 118. The Health sensors 112 can be used to measure various aspects of the user's health including heart rate, pulse, blood pressure, weight, and other factors. The proximity sensors 114 are used to identify various aspects about the user including location, and devices in the self-monitoring network 110. The environmental sensors 116 help to measure various aspects about the environment including temperature, humidity, time of day, weather and other elements. The user devices 118 includes mobile devices, tablets, smart watches and other devices close to the user, for example.

The Local Monitoring & Notification 120 environment includes a local hub 122, local sensors 124, family and neighbor devices and networks 126, and local devices 128. The local hub 122 is resident in the local environment of the user (i.e. the home) and typically connected through a router or other device to a local network. Local sensors 124 are used to identify various aspects about the local network 120 including local devices 128, the status of such devices, available family and neighbors 126 and other sensors. The local devices 128 includes mobile devices, tablets, PCs, smart TVs, and other smart devices.

The Remote Monitoring & Notification network 130 monitors the user while at the office or other common but remote location. The Remote network 130 includes a remote hub 132, remote sensors 134, coworkers 136, and remote network devices 138. Similar to the Local network, the remote hub 132, sensors 134, and remote devices 138 interact to create a network for monitoring and connecting a user and their devices to obtain data, transmit to the CAND 200, and receive notifications if appropriate (as determined by the system).

The Transition Monitoring & Notification network 140 connects the user to the system 100 during transition periods like travelling to or from work. The Transition network 140 includes a transition hub 142, transition sensors 144, passengers 146, and transition devices 148. The transition hub 140 could be a car or automotive hub and acts with the transition sensors 144 and devices 148 to connect the user during transitions.

In addition, the network 100 may include Service Provider Monitoring & Notification 150 which includes direct care providers 152, public safety 154, or public health 156 officials. The network 100 can also integrate third party data or resources 190 including real time data 192 (i.e. weather, news) and medical data 194. The sub-networks connect to the CAND system 200 to create the network 100 of the present system.

Figure 2:
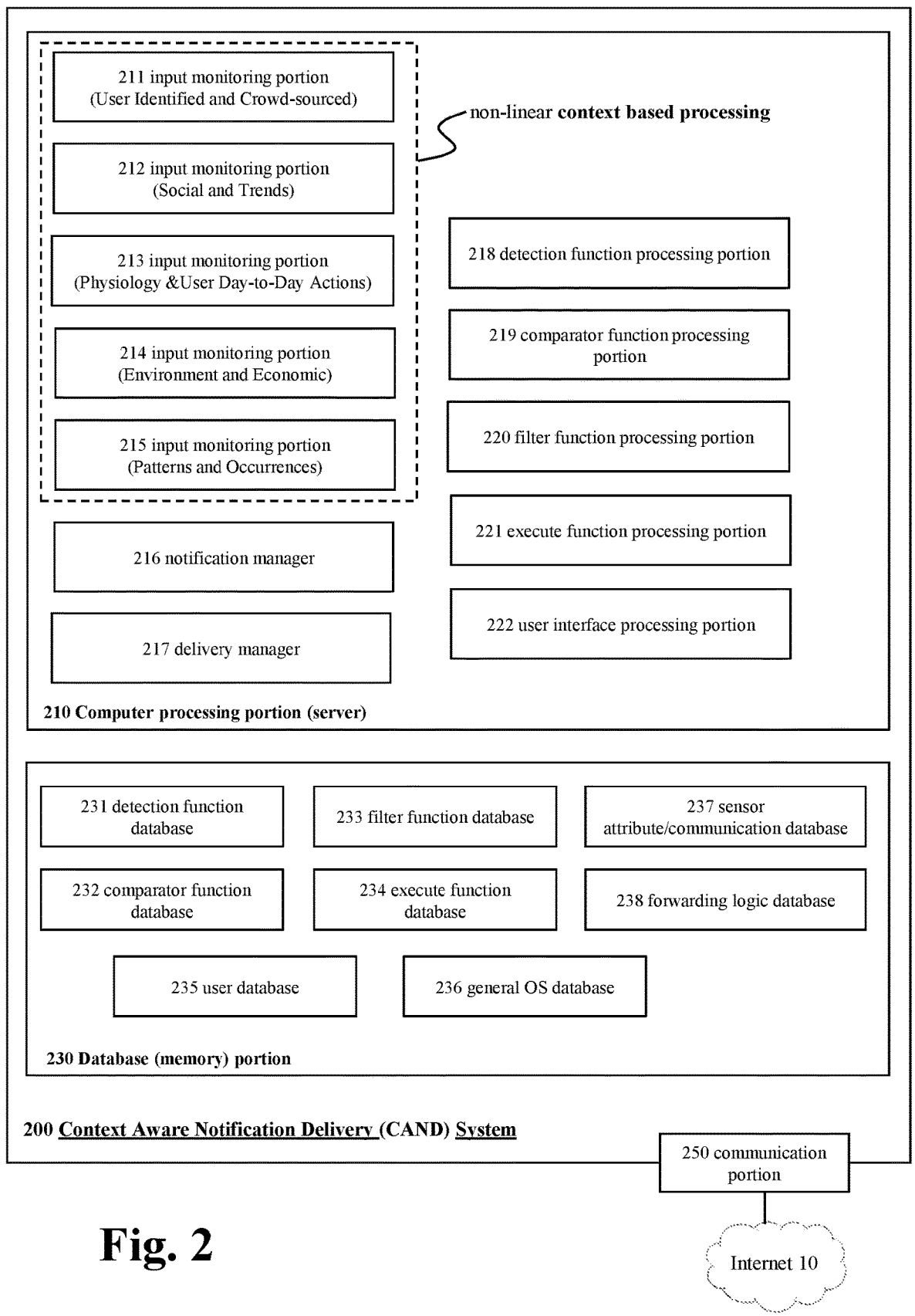
FIG. 2 is a system diagram showing details of the CAND system of FIG. 1, in accordance with at least one embodiment of the invention.

FIG. 2 is a block diagram showing details of the Context Aware Notification Delivery (CAND) system in accordance with at least one embodiment of the invention. Illustratively, the C AND system 200 includes a computer processing portion 210 and a database portion 230. The computer processing portion 210 may be constituted by one or more servers. In the situation that the computer processing portion 210 is constituted by one or more servers, such servers may be connected over a suitable network, such as the Internet. Relatedly, the system 200 includes a communication portion 250 that may support various communications to and front the system 200. As shown communication portion 250 may be connected to the Internet or connected to some other suit hie network, as may be desired.

The computer processing portion (CPP) 210 includes various processing portions. As shown in FIG. 2, the input monitoring portion 211 inputs various data that may include user identified data and/or crowd sourced data. An input monitoring portion 212 inputs various data that may include social data and/or data relating to trends. For example, the input monitoring portion 212 might input data regarding a particular health trend that the system 200 has observed in users. In one aspect of the invention, a particular health trend might be utilized to evolve or modify a particular program offered to a group of users.

As shown in FIG. 2, the CPP 200 further includes input monitoring portion 213. The input monitoring portion 213 inputs various data related to physiology and user day to day actions, in accordance with at least one embodiment of the invention.

As shown in FIG. 2, the CPP 200 further includes input monitoring portion 214. The input monitoring portion 214 inputs various environment related data and/or economic related data. For example, the input monitoring portion 214 might input data regarding current stock activity on Wall Street and adjust the handling, by the CAND system, of a particular user or group of users based on such observed stock activity.

Additionally, the CPP 210 includes input monitoring portion 215. The input monitoring portion 215 inputs a wide variety of data regarding patterns and/or occurrences. The particular nature of such data may vary widely as may be desired and/or needed for a particular user group, for example.

As reflected in FIG. 2, it is appreciated that the processing performed by the portions 211, 212, 213, 214, 215, and 216 may well be non-linear context-based processing. In other words, the processing performed need not be performed in any particular order, and the systems and methods of the invention are not limited to any particular order, but rather such processing portions may take action as enabled or invoked by the CPP 210. Such portions might take particular action based on specific external input—so as to acquire desired data. Such portions might take particular action in some periodic manner, such as hourly, daily, or weekly, for example. In general, such portions may take particular action in some predetermined manner.

As shown in FIG. 2, the CPP 210 also includes a notification manager 216 and a delivery manager 217. In accord with at least one embodiment of the invention, the notification manager may handle various processing associated with determining if a notification should be sent to a particular user. It is of course appreciated that the number of users serviced by a particular CPP 210 may well be in the hundreds, thousands, or millions. Relatedly, the CAND system 200 may well constitute many servers 210 that collectively service the various users associated with the CAND system.

With further reference to FIG. 2, the notification manager 216 performs processing so as to determine if received data constitutes a "suggested system event" as described in detail below. Further, the notification manager 216 performs processing to determine if a suggested system event is to be deemed evolved, based on additional input data, so as to result in a notification to a user. As also described below, the notification manager 216 handles related processing associated with a "cognitive window" and an "accessibility window"—both are further described in detail below.

The CPP 210 further includes a delivery manager. In accordance with at least one embodiment of the invention, the delivery manager 217, for example, handles delivery of a notification to a user—upon a suggested system event being deemed "perfected" by the notification manager 216. In some embodiments of the invention, the delivery manager 217 may simply output the notification on a communication channel that is already been determined by the notification manager. In accord with other embodiments, the delivery manager 217 may perform decisioning so as to determine a particular communication channel (perhaps selected from a group of available transmission channels) to use in forwarding the notification to the user. The latter situation reflects a scenario in which the particular communication channel utilized (or to be utilized) was not part of the decisioning of the notification manager, i.e. was not part of the decisioning as to whether or not to send the communication/notification to the user.

The CPP 210 includes further processing portions as shown in FIG. 2. In particular, the CPP 210 includes a detection function processing 218, a comparator function processing portion 219, a filter function processing portion 220, an execute function processing portion 221, and a user interface processing portion 222. The detection function processing portion 218 may perform a wide variety of tasks associated with detection of input data and/or detection of observed events, for example. The comparator function processing portion 210 may perform a wide variety of tasks related to comparing data to other data. Such comparison might include the comparison of single data points or the comparison of aggregated data. Such comparison processing may include the processing of various criteria including patterns, thresholds, summations, partial aggregation of data, and/or other criteria. The filter function processing portion may perform a wide variety of processing associated with filtering data such as filtering data relevant to system operations apart from data not relevant to system operations. The execute function processing portion 221 may handle a wide variety of processing associated with execution of tasks performed by the system 200. Further, the user interface processing portion 222 may handle a wide variety of tasks associated with interfacing with users of the system. Accordingly, the user interface processing portion 222 may provide capability to interface with a user via web browser, smartphone communication, and/or communication with any of a wide variety of other user devices and/or systems. It is appreciated that the notification manager 216 and the delivery manager 217 may well "call upon" the various processing portions 218, 219, 220, 221, 222 so as to delegate one or more tasks to such various processing portions 218, 219, 220, 221, 222.

The system 200 further includes database 230 as described above. The database may be in the form of a suitable computer readable medium or collection of computer readable media that serve to store the various wide variety of data used by and/or generated by the CPP 210 (including the various processing portions of the CPP 210 as described above). It is appreciated that the particular architecture of the CPP 210 and the particular architecture of the database 230 may be varied as desired and as is described otherwise herein. The database portion 230, in at least one embodiment of the invention, includes detection function database 231, comparator function database 232, filter function database 233, execute function database 234, user database 235, general operating system (OS) database 236, sensor attribute/communication database 237, and forwarding logic database 238. Such databases hold a wide variety of data, as such data is described below.

Figure 3:
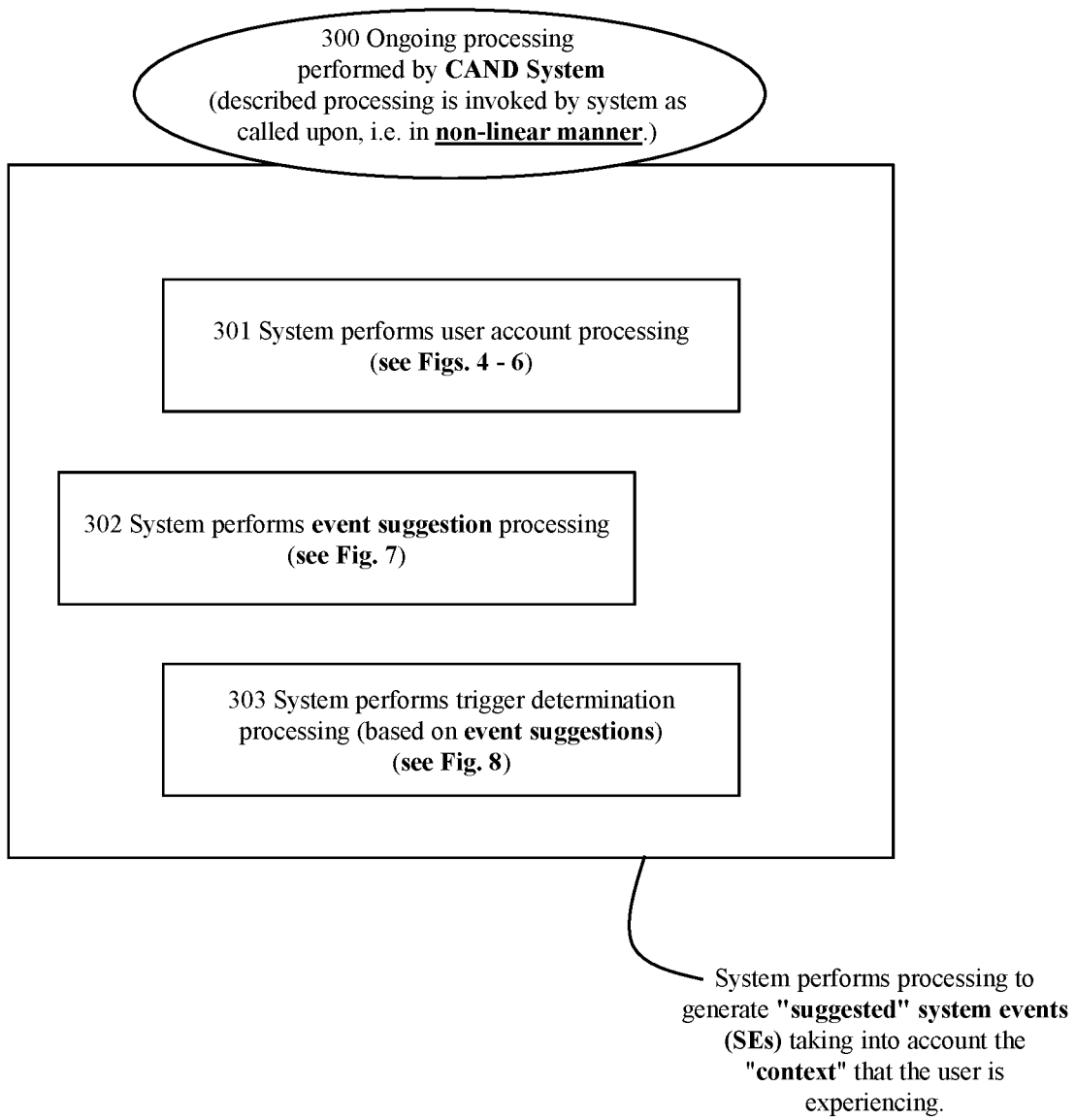
FIG. 3 is a diagram illustrating high level processing performed by the CAND system, in accordance with at least one embodiment of the invention.

FIG. 3 is a diagram illustrating processing performed by the CAND system, in accordance with at least one embodiment of the invention. More specifically, as reflected by step 300, FIG. 3 shows ongoing processing that may be performed, i.e. called upon and invoked, by the CAND system, in accordance with one embodiment of the invention. The processing shown in FIG. 3 may be performed in a non-linear manner is called upon by the CAND system. Accordingly, the invention is not limited to the particular order of processing as depicted in FIG. 3.

The ongoing processing performed by the CAND system includes step 301. In step 301, the system performs user account processing. Such user account processing may relate to on-boarding a new user to the system. On the other hand, such user account processing may include engagement with an existing user, such as to change the profile of an existing user. Further details of such processing are described below with reference to FIGS. 4-6.

The ongoing processing of FIG. 3, further includes step 302. In step 302, the system performs event suggestion processing. Various details are described below with reference to FIG. 7 in particular. In such event suggestion processing, the system observes and processes input data that is suggestive of the system performing an event.

The ongoing processing of FIG. 3, further includes step 303. In step 303, the system performs "trigger determination" processing. As reflected in FIG. 3, such trigger determination processing may, in accordance with some embodiments, be based on event suggestions that are determined in step 302. However, the invention is not limited to such linear relationship. That is, the trigger determination processing of step 303 may be done independently and without the prior "event suggestion" processing of step 302. Further details of the non-linearity of various processing of the invention are described below. Further details of the processing of step 303 are described below with reference to FIG. 8, in particular.

Figure 4:
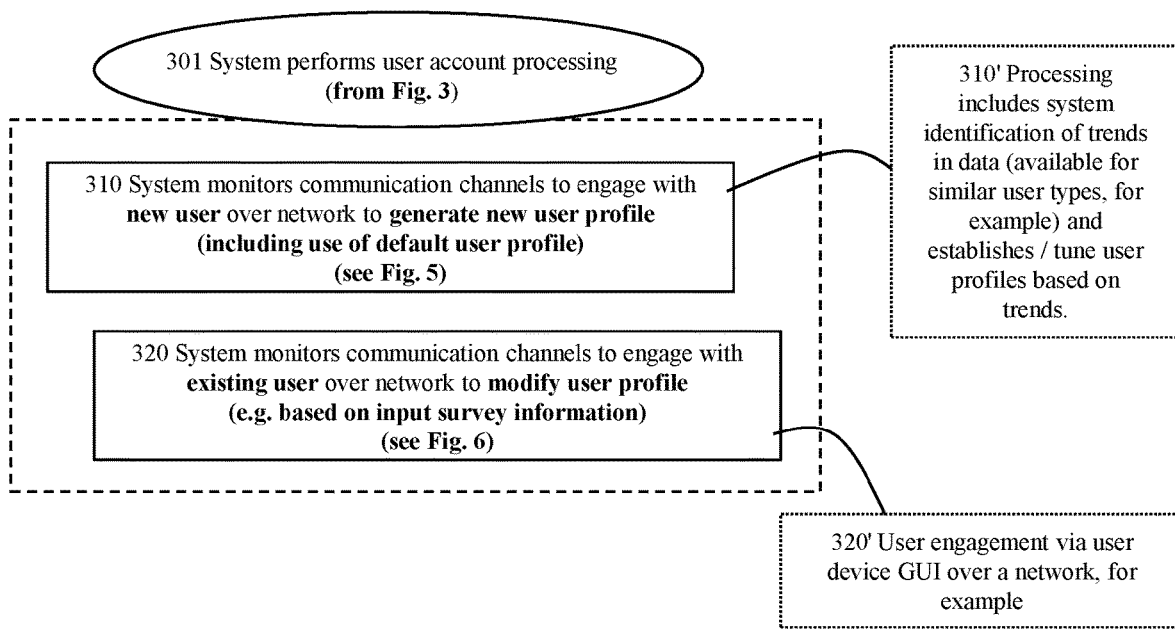
FIG. 4 is a flowchart showing in further detail "system performs user account processing" step of FIG. 3, in accordance with at least one embodiment of the invention.

FIG. 4 is a flowchart showing in further detail "system performs user account processing" step 300 of FIG. 3, in accordance with at least one embodiment of the invention. As shown, the processing of FIG. 4 includes step 310. In step 310, the system monitors communication channels to engage with a new user, over a network for example, so as to generate a new user profile. For example, the processing of step 310 might include a new user engaging with the CAND system via a web browser over the Internet, or some other network. The engagement with a new user may include the use, by the CAND system, of a default user profile. Relatedly, as reflected in box 310' of FIG. 4, the processing may include the system identification of trends and data to establish and tune user profiles based on such trends. In other words, in conjunction with inputting user profile or other data regarding a new user, the system may in one way or another map the particular attributes of the new user to existing users and/or to a particular default profile linked to a group of existing users, for example. In this processing, if the attributes of a new user are sufficiently similar to the attributes of existing users (and such existing users are commonly associated with a particular type of profile) then the new user under consideration may also be associated with that particular type of profile. Relatedly, the profile of a particular user and/or the profile associated with multiple users is "tuned" over time based on a variety of inputs including trend data. Further details are described below with reference to FIG. 5.

As shown, the processing of FIG. 4 further includes step 320. In step 320, the system monitors communication channels to engage with an existing user, over a suitable network, so as to modify the user profile of that existing user. This processing may also be performed, for example, over a network with the user interfacing with the system via a web browser. In accordance with one aspect of the processing, such engagement with an existing user or users may include the input and processing of survey information. Such survey information received from a user may be utilized to adjust or tune the profile of that particular user and/or the profile associated with other users. Further details are described below with reference to FIG. 6.

Figure 5:
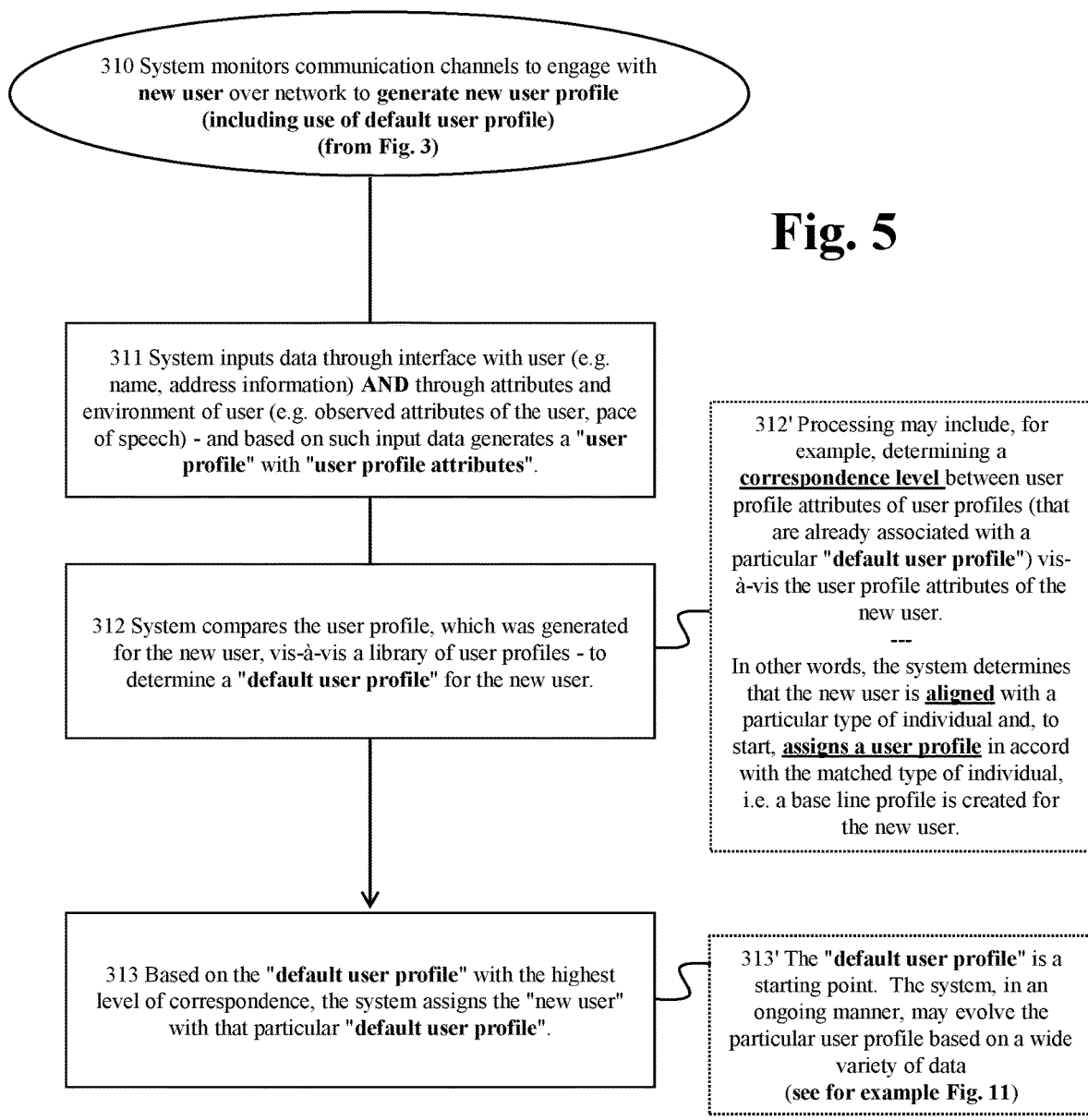
FIG. 5 is a flowchart showing in further detail the "system monitors communication channels to engage with a new user" step of FIG. 3, in accordance with at least one embodiment of the invention.

As referenced above, FIG. 5 is a flowchart showing in further detail the "system monitors communication channels to engage with a new user" step 310 of FIG. 3, in accordance with at least one embodiment of the invention. In particular, such processing includes a new user engaging with the CAND system to generate a new user profile. Such process may include the use of a default user profile. As shown, the processing starts in step 310 and passes to step 311. In step 311, the system inputs data through interface with the user. Such interface with the user may include a variety of data input over a variety of input channels. In particular, the input data may include information secured through input by the user, such as name and address information. Additionally, the input data may include data obtained regarding attributes of the user and the environment of the user. Such attributes of the user might include the pace of speech utilized by the user, particular traits of intonation used by the user, and other attributes. Data associated with the environment of the user might include the particular geographical region or the IP address utilized by the user, user device information secured by the CAND system upon the user interfacing (with the CAND system) via such user device, a call-in number utilized by the user, as well as other attributes associated with the environment user. It is appreciated that such data is illustrative and that the invention is not limited to such data. After the processing of step 311, the process passes to step 312. In step 312, the system compares the user profile, which was generated for the new user, against a library of user profiles. This processing is performed to determine a "default user profile for the new user.

As reflected at 312' of FIG. 5, such processing may include, for example, determining a correspondence level between user profile attributes of user profiles (that are already associated with a particular default user profile) vis-à-vis the user profile attributes of the new user. In other words, the processing may include the system determining that the new user is "aligned" with a particular individual or aligned with a particular group of individuals. The system then, to start, assigns a user profile in accord with the matched type of individual. In other words, the CAND system effectively generates a baseline profile for the new user—to start, in accordance with at least one embodiment of the invention.

Accordingly, after the processing of step 312 FIG. 5, the process passes to step 313. In step 313, the CAND system, based on the default user profile with the highest level of correspondence, assigns the new user with that particular default user profile. As described above, the default user profile is a starting point. The system, in an ongoing manner, may evolve the particular user profile based on a wide variety of data.

FIG. 6 is a diagram showing in further detail the "system monitors communication channels to engage with an existing user to modify user profile, step 320 of FIG. 3, in accordance with at least one embodiment of the invention. It is appreciated that such engagement between the CAND system and a user may be performed over a suitable network, such as the Internet. In particular, the processing of FIG. 6 relates to how the user profile is "tuned" in an ongoing manner. It is appreciated that the processing of FIG. 6 may be performed in a non-linear manner as such processing is called upon and invoked by the CAND system.

In general, the processing of FIG. 6 includes the CAND system engaging with existing users, securing information regarding those existing users, tuning the system based on such further secured information, and adjusting user profiles based on such further secured information. Accordingly, in step 321 of FIG. 6, the CAND system periodically reaches out to users to invite feedback regarding disposition of such users. Such feedback might include an overall indication of the mood level of the user, whether the user is happy or sad, a stress level of the user, food items consumed by the user, and/or other attributes of the user. Such input may be secured through presenting survey questions to the user.

The processing of FIG. 6 further includes step 322. In step 322, the system determines whether the feedback that is received from the user is consistent with the current handling of the user. Illustratively, the system may determine whether feedback received from a particular user is consistent with a program that such user is currently enrolled in. For example, a user might be associated with a particular program for diabetes—which requires a particular diet. The system might input data from the user regarding items consumed, by the user, that are inconsistent with such program. In response to such input information, the CAND system might simply alert the user that the consumed food is inconsistent with their current program. However, the CAND system may indeed affect a switch of programs based on the new data. Such switch of programs might be performed through dialogue and prompt with the user and/or performed in some automated manner. Accordingly, as reflected in step 323, if feedback from the user is inconsistent with the current handling of the user, then the system may adjust to address the user's changing needs and/or how user is observed to react to the system.

As shown in step 324 of FIG. 6, the CAND system may also perform a type of extrapolation processing. More specifically, a change applied to a user (based on feedback from that user and others) may then be applied to other similarly situated users. That is, changes in the profile of a user might be extrapolated to other similarly situated users.

Figure 7:
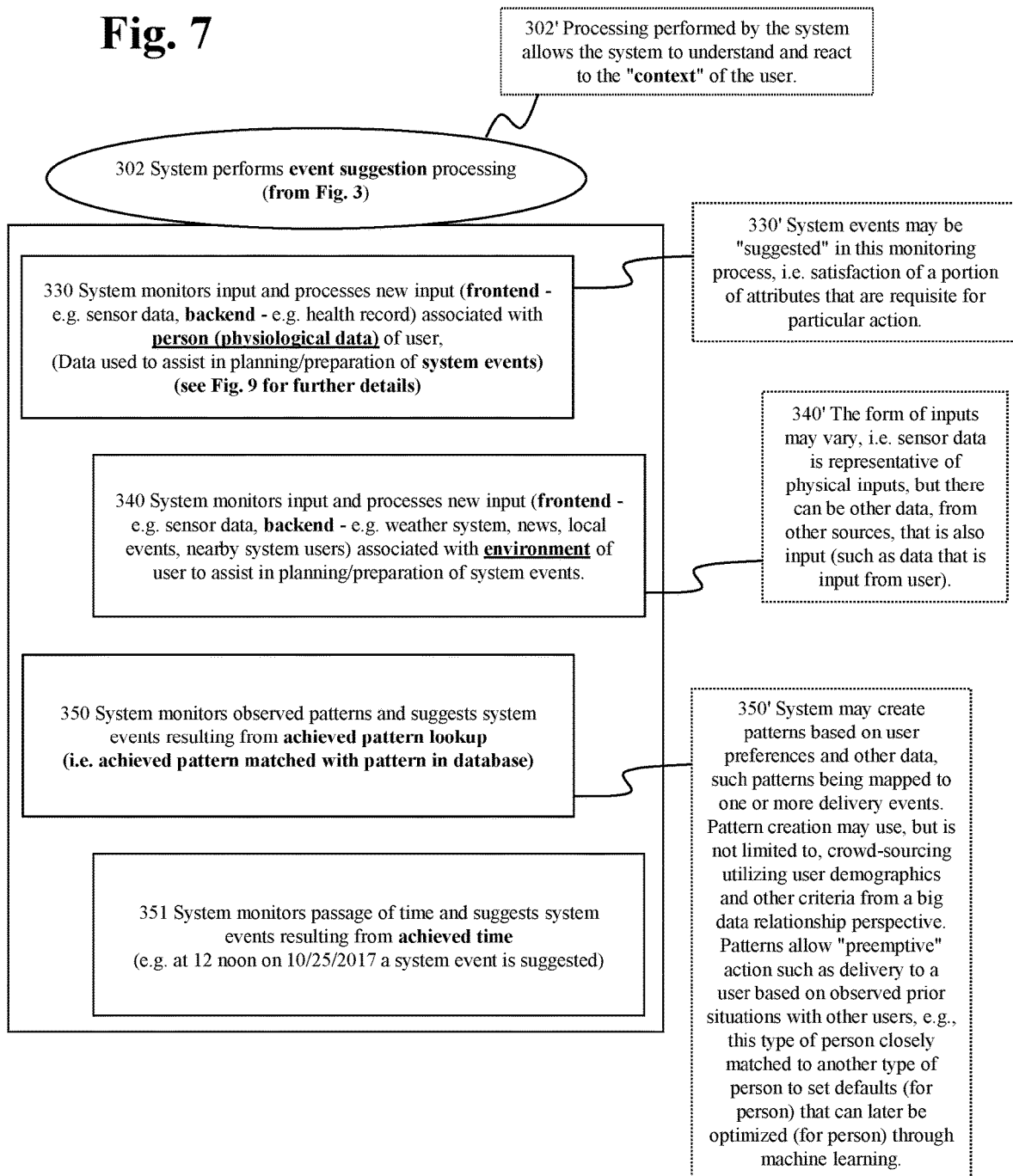
FIG. 7 is a flowchart showing in further detail the system performs event suggestion processing step of FIG. 3, in accordance with at least one embodiment of the invention.

FIG. 7 is a flowchart showing in further detail the system performs event suggestion processing step 302 of FIG. 3, in accordance with at least one embodiment of the invention. In general, as shown 302', the processing performed by the system allows the system to understand and react to the "context" of the user. The processing of FIG. 7 need not be performed in any particular linear manner—but rather may be performed as called upon and invoked by the CAND system.

The event suggestion processing of FIG. 7 includes step 330. In step 330, the system monitors new input and processes new input that is associated with the person of the user, i.e. physiological data of the user. The input may include a wide variety of data from a wide variety of sources. For example, the data may include sensor data that might be characterized as front-end data. On the other hand, the data may include health record data that might be characterized as backend data. The data secured in the processing of step 330 is utilized to assist in the planning and preparation of system events of the system. Further details of the processing of step 330 (of FIG. 7) are described below with reference to FIG. 9.

In further explanation of the processing of step 330, as shown at 330', system events may be "suggested" in this monitoring process. In other words, the data that is input, from one or more sources, may serve to satisfy a portion of attributes that are requisite for a particular action by the system, i.e. that are requisite for a particular system event by the CAND system. Illustratively, a particular system event may require the system to observe three particular types of input data. If indeed the system observes 2 out of those 3 particular types of input data, such may be interpreted by the system as constituting a suggestion of a system event. In embodiments of the invention, the CAND system then saves that "suggestion" of a system event in a suitable manner, such as in a queue. The system then does not need to re-process the determination—that the original input data (previously input) generated the suggestion of the system event. Rather, the CAND system just looks, in accordance with one embodiment, for that third requisite data input to be observed by the system. Upon such third data input being observed by the system, the CAND system then moves on to performing the particular system event. Accordingly, the systems and methods of the invention solves a technical problem of conserving computer processing bandwidth. Such computer processing bandwidth translates into both time saved as well as energy saved, which would otherwise have been required to perform additional processing. Such saved energy may be critical in particular applications, such as with portable user devices.

The processing of FIG. 7 also includes step 340, in accordance with at least one embodiment of the invention. In step 340, the system monitors input and processes new input associated with the environment of the user. This input is used in planning and preparation of system events of the CAND system. Accordingly, the processing of step 340 reflects the input of data relating to the environment in which the user is disposed, rather than the person of the user. In such manner, the processing of step 340 is distinct from the processing of step 330.

The input of data in step 340 may include the input of front-end data, such as sensor data. On the other hand, the input of data in step 340 may include the input of backend data. For example, such backend data may include weather system data, news related data, data regarding local events, and/or data regarding nearby system users. Accordingly, the data input of step 340 includes data related to the environment of the user. In further illustration, the data input in step 340 might include data from temperature sensors in the environment of the user or in some other way related to the user. Accordingly, as reflected at 340' of FIG. 7, the particular form of input data may vary. For example, sensor data represents physical inputs, but there may be other data, from other sources, that is also input. Indeed, such data may be input from the user himself. Further, it is appreciated that the distinction between the type of data input in step 330 and the type of data input in step 340 is illustrative. In some embodiments of the invention, data that is input may be related to both the person of the user, i.e. physiological data, as well as related to the environment of the user.

The processing of FIG. 7 further includes step 350, in accordance with at least one embodiment of the invention. In step 350, the system monitors observed patterns (or more generally observed criteria) and suggests system events resulting from what is characterized as an "achieved pattern lookup." In other words, an achieved pattern means a pattern, which the CAND system is looking for, has indeed been achieved (or in other words observed by the CAND system.) Accordingly, such achieved pattern, which is observed, is indeed matched with a pattern in the database. More generally, in accordance with embodiments of the invention, such "achieved pattern" made more generally be an "achieved criteria."

As reflected in box 350' of FIG. 7, the system may create patterns based on user preferences and other data. Such patterns, in the CAND system, are mapped to one or more delivery events. Pattern creation may use, but is not limited to, crowdsourcing utilizing user demographics and other criteria from a big data relationship perspective, for example. Particular criteria, such as patterns, allow "preemptive" action—such as delivery to a user based on observed prior situations with other users. For example, a particular type of user might be closely matched, in attributes, to another type of person to set defaults that can later be optimized through machine learning.

The processing of FIG. 7 further includes step 351. In step 351, the system monitors the passage of time and suggests system events resulting from an achieved time. Accordingly, for example, the processing of step 351 relates to a situation in which a particular system event is scheduled for a particular date and/or time.

Figure 8:
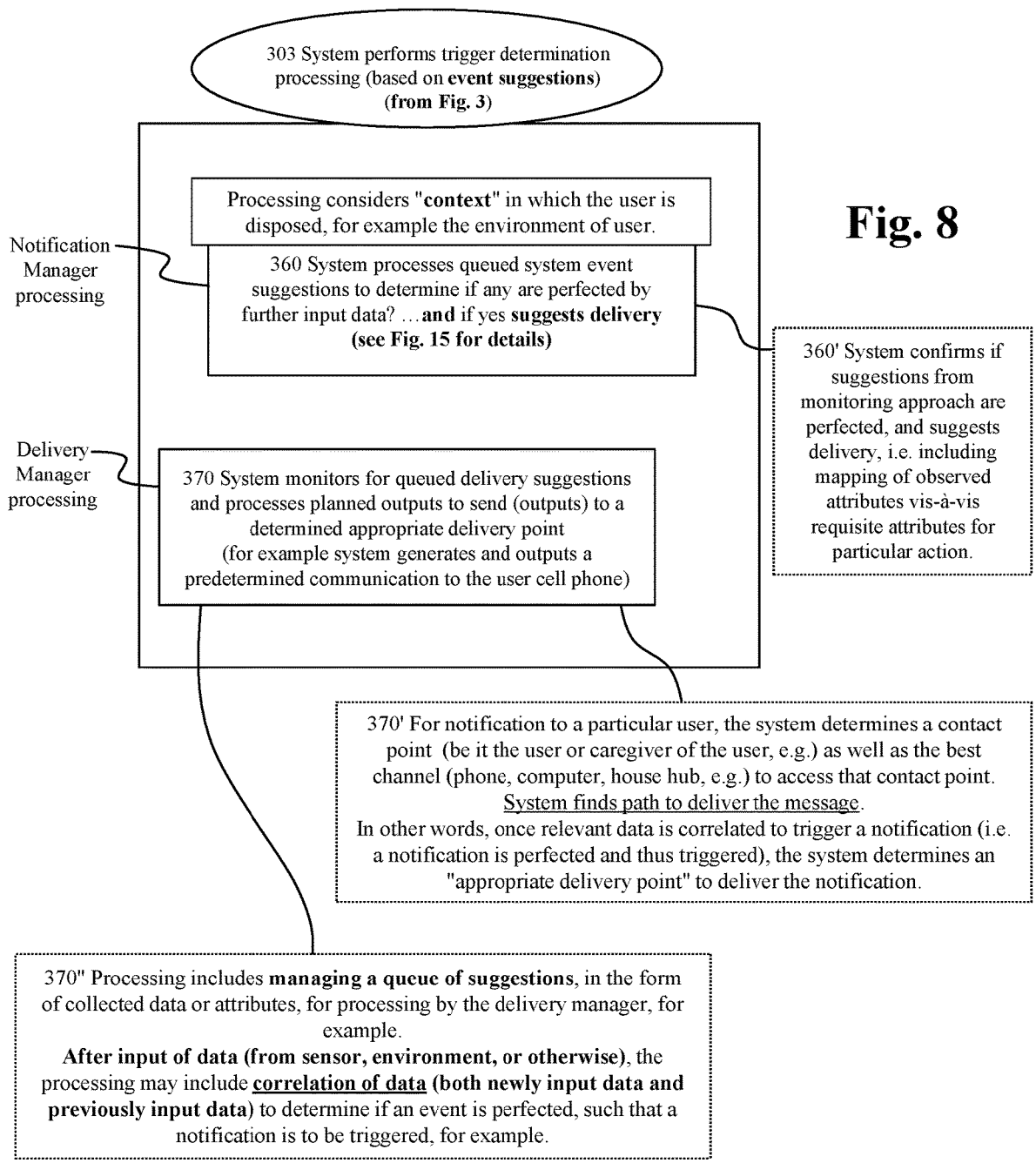
FIG. 8 is a flowchart showing in further detail the "system performs trigger determination processing (based on event suggestions) step of FIG. 3, in accordance with at least one embodiment of the invention.

FIG. 8 is a flowchart showing in further detail the "system performs trigger determination processing (based on event suggestions) step 303 of FIG. 3, in accordance with at least one embodiment of the invention. The processing of step 303 of FIG. 8 includes step 360. In step 360, the system processes queued system event suggestions to determine if any suggestions are "perfected" by further input data. If any system event suggestions have indeed been perfected, then the CAND system suggests delivery. Such processing is described in further detail below. Accordingly, as reflected in box 360', the system confirms if suggestions from monitoring have indeed been perfected. If any suggestions have indeed been perfected, then the CAND system suggest delivery. Such processing may include mapping of observed attributes vis-à-vis the requisite attributes for particular action. As reflected in FIG. 8, the processing of step 360 may be performed by a notification manager, in accordance with one embodiment of the invention. The processing of FIG. 8 also includes step 370. In step 370, the system monitors for queued delivery suggestions and processes planned outputs to send (i.e. output) to a predetermined appropriate delivery point. For example, the system generates and outputs a predetermined communication, based on observed data, to a user cell phone. Such processing may be performed by a delivery manager as reflected in FIG. 8.

As shown in box 370' of FIG. 8, for notification to a particular user, the system determines a contact point as well as a best channel, i.e. a communication channel, to access the contact point. The contact point might be a user or a caregiver of the user, for example. Further, the best channel, i.e. communication channel, might be a phone, computer, household, or some other communication channel. In summary, the system finds a path to deliver the particular message to the user. In other words, once relevant data is correlated to trigger a notification (i.e. a notification is perfected in this trigger), the system determines an appropriate delivery point to deliver the notification, in accordance with at least one embodiment of the invention.

As shown in box 370" of FIG. 8, the processing performed by the CAND system may include managing a queue of suggestions for processing by the system. For example, such processing may be performed by the delivery manager portion of the system, for example. Further, the queue of suggestions might be in the form of collected data or attributes. After input of data (from sensor, environment, or otherwise) the processing may include correlation of data to determine if an event is suggested or perfected. If an event is indeed found to be perfected, then a notification to the user may be sent. Such correlation of data may include both newly input data and previously input data. In other words, the previously input data may well have "suggested" a system event. Then, based on newly input data, that suggested system event is transformed into a perfected system event. Such "perfected" system event then results in a notification being sent to a user or someone associated with the user.

Figure 9:
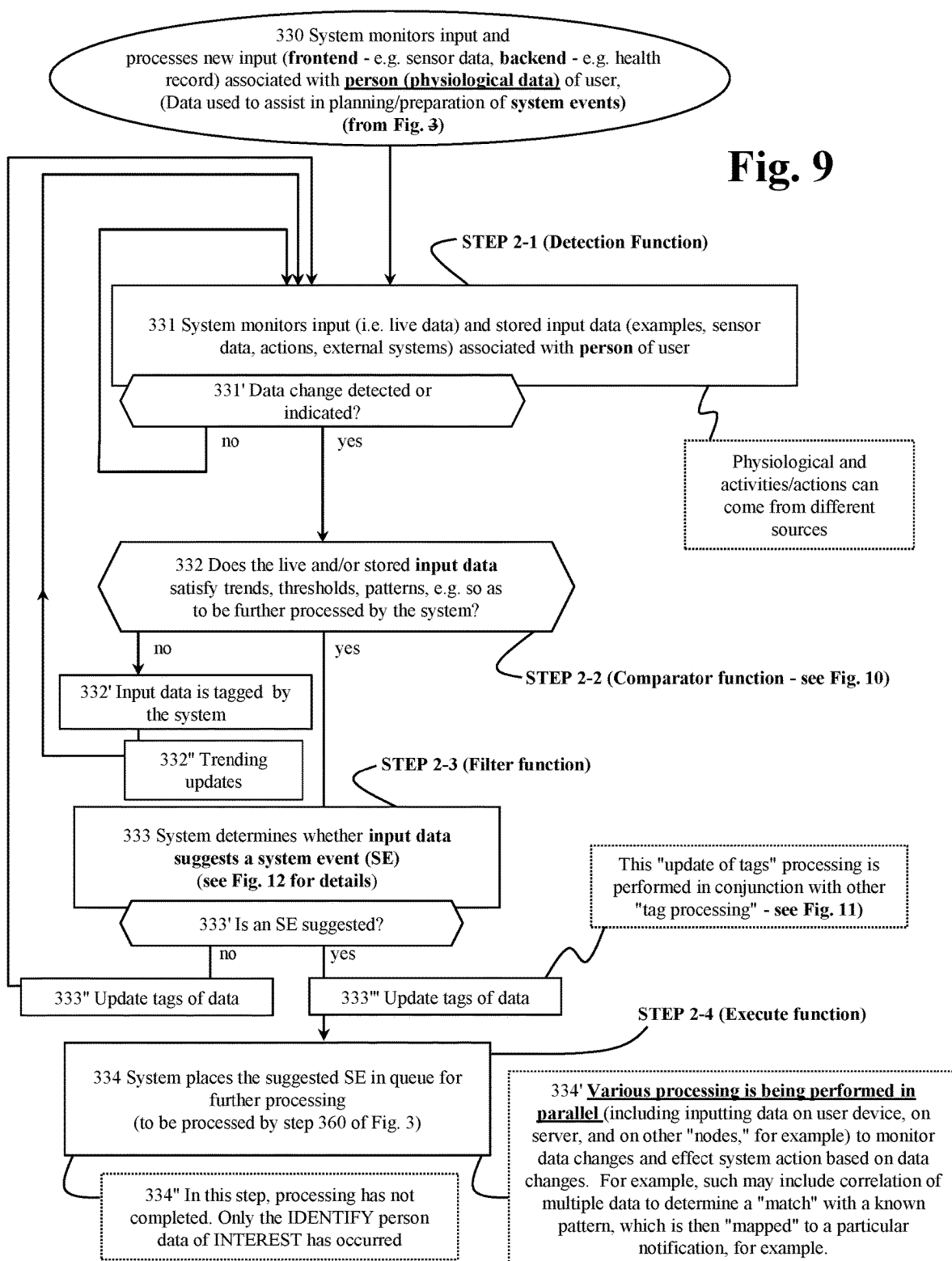
FIG. 9 is a flowchart showing in further detail the system monitors input and processes new input associated with the person of the user, step of FIG. 3, in accordance with at least one embodiment of the invention.

FIG. 9 is a flowchart showing in further detail the system monitors input and processes new input associated with the person of the user, step 330 of FIG. 3, in accordance with at least one embodiment of the invention. As described above, the processing of FIG. 9 might include front end data such as sensor data, as well as backend data such as health record data. Such processing relates to physiological data associated with the person user. Such data is used to assist in planning and preparation of system events of the CAND system. As shown in FIG. 9, processing starts in step 330 passes to step 331. In step 331, the system monitors input and stores input data associated with the person of the user. Such input may well be currently input data. Further, the stored input data might for example, be sensor data, current or prior actions of the CAND system, and/or current or prior actions by external systems. In general, the processing of step 331 waits for data to be input. Accordingly, as reflected in step 331', decisioning is performed of whether a data change is detected or in some way indicated, for example. If no, then the processing merely loops back to step 331 to perform further waiting. Step 331 may be characterized as a STEP 2-1 (Detection Function).

On the other hand, if yes in step 331', then the processing passes to step 332. In step 332, the system determines whether the live (i.e. current) input data and/or stored input data satisfies criteria such as trends, thresholds, patterns, for example, so as to be further processed by the system. In other words, in step 332, the system attempts to understand whether there is any meaning to the data as the data is being observed, be that data input previously or currently. If the input data does not satisfy any trends thresholds, patterns, for example, then the decisioning results in a "no" and the process passes to step 332'. In step 332', the input data is tagged by the system. Accordingly, even though no trends, thresholds, patterns were identified—any newly input data is still tagged in accordance with one embodiment of the invention—so as to be more effectively used in subsequent processing. Additionally, as reflected in step 332", such data as tagged may contribute to trending updates and/or other aggregated data processing. After the processing of step 332", the processing then passes back to step 331. Step 332 may be characterized as a STEP 2-2 (Comparator function—see FIG. 10).

On the other hand, it may be determined in step 332 that the live input data and/or stored input data does indeed satisfy trends, thresholds, patterns, for example. Accordingly, the process results in a "yes" in step 332—and the processing passes to step 333. In step 333, the system determines whether the input data suggests a system event (SE). Further details are described with reference to FIG. 12. Step 333 may be characterized as a STEP 2-3 (Filter function). If the decisioning in step 333' results in a "no", then the CAND system updates the tags associated with the data (step 333") and the process passes back to step 331 to wait for additional data. On the other hand, the determination in step 333' may indeed be yes. Accordingly, the system updates the tags associated with the data, but then, rather than returning to step 331, the processing passes to step 334. In step 334, the system places the suggested system event in queue for further processing. More specifically, such further processing means that the data is to be processed by step 360 of FIG. 3.

As reflected by box 334' of FIG. 9, various processing of the CAND system is being performed in parallel so as to monitor data changes and/or effect system action based on those data changes. Such parallel processing may include the inputting of data from a user device onto a server, and/or onto or from other "nodes" of the system. To effect system action based on data changes might include, for example, correlation of multiple data to determine a "match" with known criteria, e.g. pattern. These criteria are then "mapped" to a particular notification, for example, in accordance with at least one embodiment of the invention.

As reflected in box 334" of FIG. 9, the processing of step 334 is merely a step that is to be followed up by subsequent processing. Step 334 may be characterized as a STEP 2-4 (Execute function). In other words, the processing of step 334 relates to the identification of data of interest relating to the person of the user, i.e. physiological data for example—but does not terminate the processing—in that it is to be determined what action, if any, is to be taken by the CAND system based on the identification of the personal data that is of interest.

FIG. 10 is a diagram showing further details of "comparative" processing performed by the CAND system, in accordance with at least one embodiment. As shown in FIG. 10, the comparator functions may include more than just limited threshold detectors. Also, trending, patterns, including nonlinear dynamics and chaos theory like Correlation Dimension "CD" among others. In accordance with one embodiment the invention, comparator processing may use and/or require metadata tags for follow-up reviews. In particular, such follow-up reviews may include subsequent processing of data to assess correlation of data, for example.

To explain further, essentially, the comparative processing of the invention is looking to see if a system event should be queued based on some earlier criteria for selection. For example, a too high, too low, spike, large difference, etc. style of scenario is detected by the system. As otherwise described herein, such processing addresses a technical problem of reducing battery consumption and/or bandwidth consumption. In particular, the consumption of battery may be critical in the processing in whole or in part that is performed on a user device such as a phone. Further, the consumption of bandwidth may be critical in certain network environments. In general, the processing performed by the invention allows the CAND system to operate in a highly efficient manner conserving both processing consumption, battery consumption, and network bandwidth consumption, for example.

FIG. 11 is a diagram showing further aspects of tagging data, in accordance with at least one embodiment of the invention. As illustrated, tagging data serves a variety of purposes. For example, tagging data serves to preserve knowledge of the system regarding the data. In particular, tagging of data allows particular attributes of data to be preserved and accessed in a highly efficient manner. The tagging of data serves to correlate such data with other data so as to identify and/or understand patterns or trends, for example. Such correlation of data me be performed in a particular timed manner as desired, such as in a particular periodic manner and/or upon the introduction into the system of new related data. Tagging data further serves to understand duplicate data and/or stagnant data. For example, a tag associated with newly input data that is mutually exclusive to a tag associated with older data may result in the older data being deleted from consideration. Further, as shown in FIG. 11, the tagging of data serves to, in general, assist in storing and archiving data for current and/or later use. It is appreciated that the general use of tagging data is known in the art. However, the systems and methods of the invention leverage the tagging of data in a novel manner so as to effectively communicate with a user based on a context experienced by that user.

Figure 12:
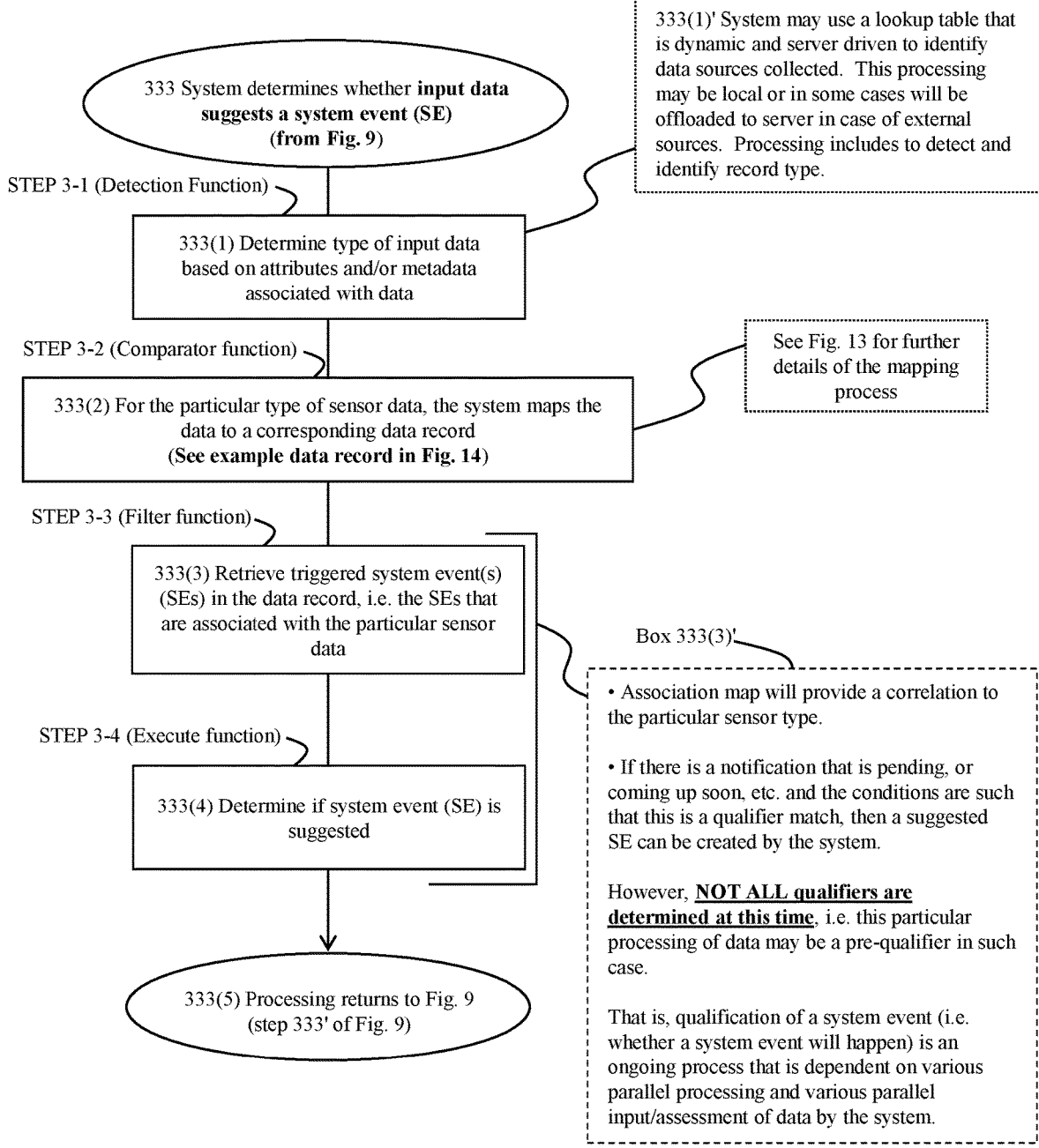
FIG. 12 is a flowchart showing in further detail the "system determines whether input data suggests a system event" step of FIG. 9, in accordance with at least one embodiment of the invention.

FIG. 12 is a flowchart showing in further detail the "system determines whether input data suggests a system event" step 333 of FIG. 9, in accordance with at least one embodiment of the invention. In particular, in accord with the example of FIG. 12, the input data is constituted by sensor data, in this example. As shown, the process starts in step 333 and passes to step 333(1). In step 333(1), the processing determines the particular type of input data based on attributes and/or metadata associated with the particular type of data. For example, attributes associated with the data may be indicative that the data was sourced from a particular type of sensor. Step 333(1) may be characterized as a STEP 3-1 (Detection Function). After the processing of step 331-1, process passes to step 333(2). In step 333(2), for the particular type of sensor data, the system maps the data to a corresponding data record. For example, FIG. 14 shows an example data record. Additionally, FIG. 13 shows further details of a mapping process, in accordance with one embodiment of the invention. Step 333(2) may be characterized as a STEP 3-2 (Comparator function).

As reflected in box 333(1)' of FIG. 12, the system may use a lookup table that is dynamic, and server driven to identify data sources collected. This processing may be local or in some cases may be offloaded to a server. Such processing includes the detection and identification of record types, in accordance with at least one embodiment of the invention.

After the processing of step 333(2), the process passes to step 333(3). In step 333(3), the processing retrieves any triggered system events (i.e. suggested system events) that are associated with the data record, which was mapped to. In other words, in accordance with one aspect of the invention, the processing maps the input data to a particular record—and that data record contains data regarding a particular system event that is dictated by the particular sensor data. It is appreciated that such processing may well involve thresholds and/or other criteria to determine whether data of certain value does or does not result in a system event. Step 333(3) may be characterized as a STEP 3-3 (Filter function). Accordingly, in step 333(4), the system determines if a system event is indeed suggested by the input data. Step 333(4) may be characterized as a STEP 3-4 (Execute function). Then, the process passes to step 333(5). In step 333(5), the processing returns to FIG. 9—and specifically returns to step 333' of FIG. 9.

As is reflected in FIG. 12, in box 333(3)', an association map may provide a correlation to the particular sensor type. In other words, if there is a notification that is pending, or coming up soon, etc.—and the conditions are such that this is a qualifier match—then a suggested system event can be created by the system. In other words, what is meant by the conditions are such that the newly input data is a qualifier match—means that a system event is "perfected". In other words, data has been received to fully support a system action. This is distinct from a system event being "suggested" by the input data. In the situation where system event is suggested by the input data, this means that the data is still lacking so as to fully support a system event. However, the data is indeed sufficient so as to place a "suggested" system event into queue for processing. This is the processing that provides the efficiencies of the system—such as when the final piece of "qualifying" data is received, the system may then efficiently move on to performing the system event, i.e. in that a suggested system event has been perfected.

As is also reflected in box 333(3)', not all qualifiers are determined in conjunction with the processing of FIG. 12. Indeed, processing data may be a pre-qualifier. In other words, qualification of a system event (i.e. whether a system event will happen) is an ongoing process that is dependent on various parallel processing and various parallel input/assessment of data by the system.

FIG. 13 is a diagram showing aspects of data record mapping in accordance with at least one embodiment of the invention. In other words, such "data record mapping" means that a data record is "mapped to" based on a particular type of data being input by the system. For example, the particular type of data may be sensor data. The data record, which is mapped to, then provides instructions to the system regarding what action is to be taken based on the currently input data as well as based on the previously input data. For example, the processing may include data record mapping including comparisons, limits, trends, chaos theory, multiples, etc.—as well as based on what are the changing conditions that can spur a suggested system event. For example, such processing might include the delta change from previous condition. For example, it may be the situation the last heart rate was 90 BPM, but has dropped to 60 BPM. This sudden decrease, observed by the system, may mean that stress has been reduced. Further, it is appreciated that conditions that can spur suggested action by the system may indeed change over time. This is true, in particular, for certain users. The system is able to understand and react to such changing conditions in that the system understands the "context" in which the user is disposed. For example, it may be the situation that the system learns that a particular user is an athlete and adjusts threshold beats per minute (bpm) thresholds based on such learned data.

FIG. 14 is a diagram showing a computer table 1400 with data records 1401 in accordance with at least one embodiment of the invention. As shown, the record 1401 includes record identifier data, observed sensor data, pre-qualifier types of data, and pre-qualifier data. As reflected in box 1400'—data table 1400 with record 1401 is provided as an example in the context of the processing of FIG. 12, for example. It is appreciated that for other comparative functions, the system may utilize various additional tables with metadata references between tables, for example. In general, various data structures might be utilized, including relational databases and other data structures.

Figure 15A:
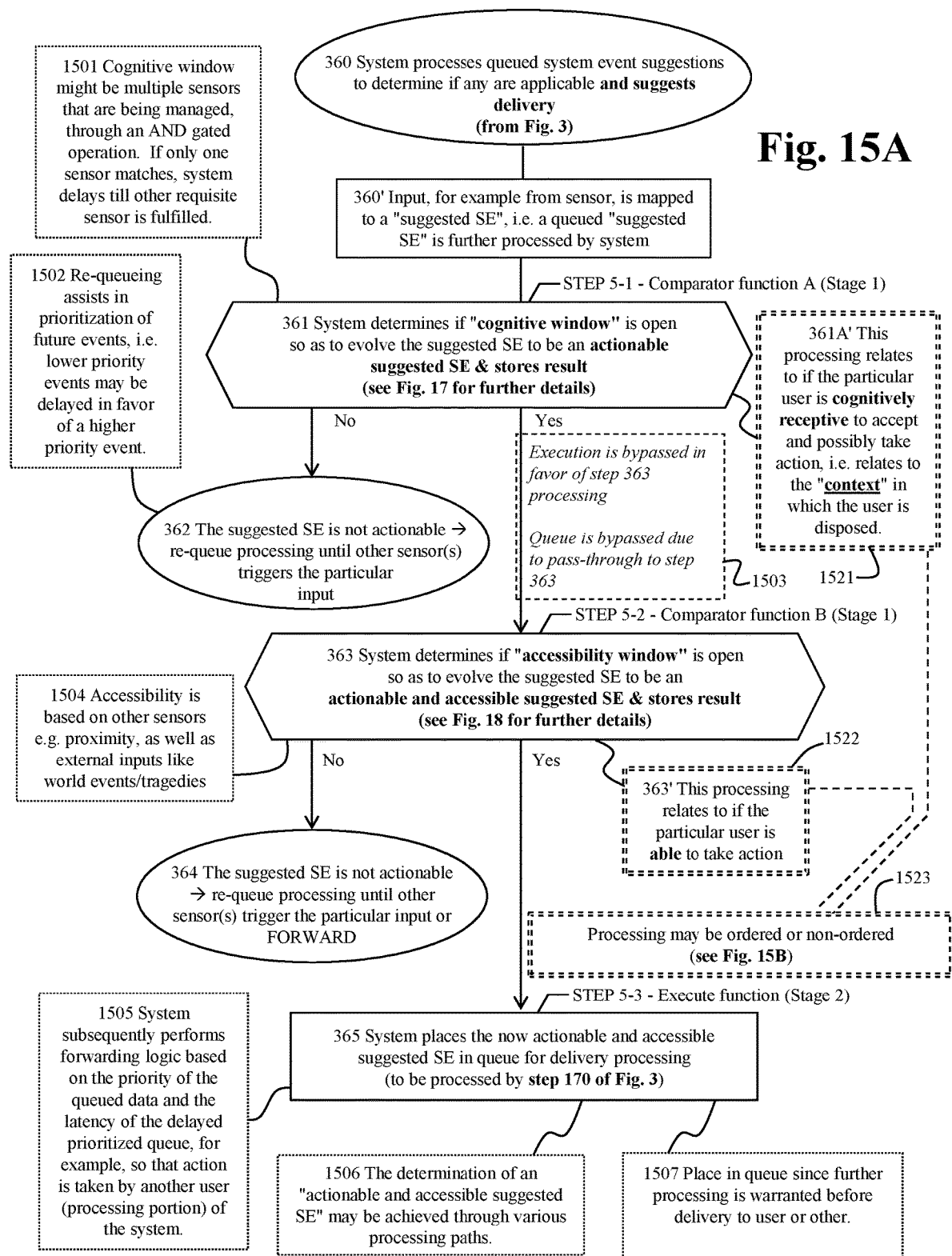
FIG. 15A is a flowchart showing in further detail the system processes queued system event suggestions to determine if any are applicable and suggests delivery, step 302 of FIG. 3, in accordance with at least one embodiment of the invention.

FIG. 15A is a flowchart showing in further detail the system processes queued system event suggestions to determine if any are applicable and suggests delivery, step 360 FIG. 3, in accordance with at least one embodiment of the invention. As shown, the process starts in step 360 and passes to step 360'.

In step 360', input from a sensor, for example, is mapped to a suggested system event. In other words, a suggested system event (resulting from prior input data) has been previously placed into queue. The newly input data, input in step 360', is associated with such queued suggested system event so as to result in further processing of such queued system event. After the mapping of step 360', the process passes to step 360. In step 361, the system determines if a "cognitive window" is open so as to evolve the suggested system event to be an actionable suggested system event. The processing then stores the result. Step 361 may also be characterized as a STEP 5-1—Comparator function A (Stage 1).

In other words, the processing of step 361 determines if a suggested system event has evolved into an actionable suggested system event. To explain further, the concept of a suggested system event being evolved means, in accord with one embodiment, that inputs have been received so as to transform a suggested system event to an actionable system event that may be performed by the system. For example, as reflected in box 1501, a cognitive window might be fulfilled by multiple sensors that are being managed through an AND gated Boolean operation. In this example, if only one sensor input matches, then the system will delay until the other requisite sensor is fulfilled. In other words, if a particular system event requires specific data type from two respective sensors, and only one sensor requirement is fulfilled—then such situation may constitute a "suggested system event". This suggested system event will then be placed into queue. At a later point in time, the other sensor requirement may be fulfilled. This newly input data is then compared to the suggested system event in queue—so as to evolve the suggested system event into an actionable system event. The actionable system event is actionable in that the system will put into motion the processing to perform the perfected system event, but only assuming that the suggested system event is also an accessible system event. Relatedly, as reflected in box 1502 of FIG. 15A, such described re-queuing assists in prioritization of future events. That is, lower priority events may be delayed in favor of a higher priority event. Accordingly, the decision of step 361 may result in a "no" determination. As a result, the processing passes from step 361 to step 362. This means that the suggested system event is not actionable. Accordingly, the particular suggested system event will be re-queued until one or more sensors trigger the particular input that is required to evolve the suggested system event to an actionable system event. There may well be multiple suggested system events in queue in the system, in parallel, that will result in one and the same actionable system event. The processing of step 361 is further described further below with reference to FIG. 17.

If a suggested system event is deemed to have evolved into an actionable system event AND a suggested system event is deemed to have evolved into an accessible system event—then the system deems that the system event has evolved into a perfected system event. In accordance with some embodiments, the evolution of such a suggested system event may or may not include particulars of the delivery mechanism, such as the particular communication channel utilized for the delivery. In other words, if the evolution of the suggested system event "factors in" the particular communication utilized in the delivery of the notification—then there may be no more decisioning performed by the CAND system—for such notification to be sent (absent available system resources, for example). On the other hand, the processing of the CAND system may utilize an approach in which they suggested system event is indeed deemed to be "perfected" but with the actual performance of the system event being contingent on such things as communication logistics, such as does the CAND system have electronic resources so as to actually send the notification to the user or someone associated with the user, for example.

With further reference to FIG. 16, the determination of step 361 may determine that indeed the cognitive window is open so as to evolve the suggested system event to be an actionable suggested system event. However, as reflected in box 1503 FIG. 15A, execution of the actionable suggested system event is bypassed in favor of the step 363 processing. Further, any queuing is also bypassed due to the pass-through of the processing to step 363. In other words, even though the suggested system event has been deemed (in step 361) to be an actionable system event, such suggested system event has not been perfected—since the suggested system event has not yet been deemed to be an accessible system event (i.e. the processing of step 363 has not yet been performed).

That is, in step 363 of FIG. 15A, the system performs processing to determine if an "accessibility window" is open so as to evolve the suggested system event to be an actionable AND an accessible suggested system event, i.e. a "perfected system event". As reflected in box 1504, accessibility may be (or may not be) based on other or different inputs/sensors vis-à-vis the inputs/sensors utilized in conjunction with the cognitive window processing. For example, accessibility might be based on proximity sensors as well as external inputs like world events or tragedies. Further details of the processing of step 363 are described below with reference to FIG. 18. Step 363 may also be characterized as a STEP 5-2—Comparator function B (Stage 1).

If the determination is "no" in step 363, then the processing passes to step 364. In step 364, the system deems that the suggested system event is not actionable. As a result, processing of the suggested system event is re-queued until other input, such as other sensor input or backend record input, triggers the particular queued suggested system event.

On the other hand, the determination may be "yes" in step 363. As a result, the processing passes from step 363 to step 365, as shown in FIG. 15A. In step 365, the system places the now deemed actionable accessible suggested system event in queue for delivery processing. Step 365 may also be characterized as a STEP 5-3—Execute function (Stage 2). For example, such processing may be performed as reflected in step 170 of FIG. 3. As reflected in box 1505, in accordance with one embodiment, the system subsequently performs forwarding logic based on the priority of the queued data and the latency of the delayed prioritized queue, for example. Such action may be taken by another user (another processing portion) of the system. As reflected in box 1506 of FIG. 15A, the determination of an actionable and accessible suggested system event may be achieved through various processing tasks. What this means, in one aspect, is that there may well be multiple suggested system events that are in queue, that may result in particular action by the system, such as a particular notification to the user. If any of those suggested system events are perfected, such as by additional data being observed by the system, then the particular notification may be sent. Relatedly, the processing may include reconciliation of multiple perfected system events—such that only one notification is indeed sent.

As also reflected in FIG. 15A, even though the processing of step 365 places the now actionable and accessible suggested system event in queue for delivery processing—further processing may still be warranted before delivery to the user or to another person associated with the user, such as a caregiver.

As described at 1521 of FIG. 15A, the processing of step 361 determines if the cognitive window is open so as to evolve the suggested system event to be an actionable suggested system event and stores the result. On the other hand, the processing of step 363 determines if the accessibility window is open so as to evolve the suggested system event to be an actionable and accessible suggested system event, i.e. a perfected system event. As shown at box 1523, such processing is not necessarily ordered as shown in FIG. 15. That is, FIG. 15B is a flowchart showing such processing in reverse manner to the processing of FIG. 15A, in accordance with at least one embodiment of the invention. As shown in FIG. 15B, in step 363B, the system first determines if an accessibility window is open so as to evolve the suggested system event to be an accessible system event, and stores the result. Then, in step 361B, the system determines if the cognitive window is open so as to evolve the suggested system event to also be an actionable (and accessible) suggested system event. The system then stores the result.

Furthermore, the processing of step 361 and the processing of step 363 of FIG. 15A may indeed be performed in parallel with resulting determinations generated in parallel. Such resulting determinations may then be compared so as to dictate subsequent action by the system, i.e. such that the resulting determinations collectively result in the system deeming the suggested system event being a perfected system event—thus resulting in a notification being sent to the user.

FIG. 16 is a flowchart showing further details the "system determines if cognitive window is open so as to evolve the suggested system event to be an actionable suggested system event, step 361 of FIG. 15, in accordance with at least one embodiment of the invention. The processing of FIG. 16 further illustrates (box 361') that the CAND system of the invention is "context" aware and provides such capability through non-linear input and processing of various data from various sources. An illustrative example is a situation where a user is approaching her home with a not-yet opened garage. Accordingly, in this example situation, the accessibility window might be deemed "open" by the system since the particular user is proximate to her garage in the home environment. However, in the example situation, an armed assailant has approached the user. This results in increased heart BPM, increased blood pressure, and potentially other observed attributes associated with the person of the user. In this example situation, the CAND system, via sensed inputs, recognizes that some adverse situation is occurring—or in other words, the CAND system assesses the "context" of the user based on various data. In this situation, the system recognizes that some adverse situation is occurring and, as a result, does not open the garage door so as to not expose the user's family to danger. Accordingly, while the CAND system may well have deemed the accessibility window open in this example, the system indeed deemed the cognitive window not open. Accordingly, the CAND system assessed the context of the user and took beneficial action based on such context of the user.

With further reference to FIG. 16, after the processing is initiated in step 361, the process passes to step 361(1). Step 361(1) may be characterized as Step 1—Detection of queued events. In step 361(1), the system retrieves cognitive contextual factors associated with a particular suggested system event. Then, the processing passes to step 361(2). In step 361(2), the system assigns weighting to each cognitive contextual factor based on a rule set. As a result, the system determines a weighted factor value for each cognitive contextual factor. It should be appreciated; the weighting of various cognitive contextual factors allows the CAND system to place greater emphasis on some cognitive contextual factors over other cognitive contextual factors. Relatedly, as reflected at 361(2)', each cognitive contextual factor (as weighted) may favor or disfavor the system determining that a particular suggested system event is to be deemed an actionable system event. The weighting associated with particular cognitive contextual factors may also vary over time or may vary dependent on other cognitive contextual factors. For example, it may be desired (although not necessary) for the user to take particular medication while the user is at home. In this example, there may be a particular window of time in which the user is to take her medication. The weight, in the processing of step 361(2), accorded to the user's proximity to her home may be greater at the beginning of the time window vis-à-vis the weight accorded to the user's proximity to her home at the end of the time window. Accordingly, such processing reflects the real-life context in which it would be desirable to take a particular medication while the user is at home—but at the end of that particular time (in which the user needs to take her medication) all that really matters is that the user indeed takes her medication.

After the processing of step 361(2), the process passes to step 361(3). In step 361(3), the system sums (determines a summation), for example, the various weighted contextual factor values to yield a summed weighted factor value. The invention is of course not limited to such particular mathematical processing. Rather, the processing of step 361(3) reflects that in one way or another, the CAND system collectively considers the various cognitive contextual factors that might influence the sending or not sending of a particular notification, for example. After the processing of step 361(3), the process passes to step 361(4). In step 361(4), the system further (determines whether the system event under consideration is an actionable system event. In other words, is the cognitive window open so as to deem the system event (under consideration) to be an actionable system event. In this example, such determination is performed based on comparing the sum weighted contextual factor value vis-à-vis a corresponding threshold value. The invention is also not limited to such particular processing and/or the use of such particular interrelationship as a threshold. Rather, the processing of step 361(4) reflects that various input information aggregated together (in a collective manner) is then compared to some known quantity so as to determine whether the suggested system event under consideration should be deemed an actionable system event. The systems and methods of the invention may make such determination in various ways. For example, the system processing may include aggregating some weighted values together so as to determine if such first aggregation satisfies a particular threshold value, as well as aggregating other weighted values together so as to determine if such second aggregation satisfies a second particular threshold value. Accordingly, different input values might be separately aggregated together—and then compared to some known quantity, so as to determine if a suggested system event should evolve into an actionable system event. As described above, if such actionable system event is also deemed to be an accessible system event, then such system event is deemed to be perfected—thus resulting in a notification being sent to the user.

As reflected at 1601, the processing of step 361(2), step 361(3), and step 361(4) shows processing in which cognitive related parameters are aggregated and/or mapped so as to allow the system to understand such cognitive related parameters. The processing of step 361(2), step 361(3), and step 361(4) may be characterized collectively as Step 2—comparator functions. Further details are described below with reference to FIG. 17.

After the processing of step 361(4), the process passes to step 361(5). In step 361(5), the system stores the determination of whether the cognitive window is open or whether the cognitive window is not open. Step 361(5) may also be characterized as Step 3—filtering. Then, the processing passes to step 361(6). In step 361(6), the processing returns to FIG. 15A. Specifically, the processing passes to either step 362 (if the cognitive window is not open) or step 363 (if the cognitive window is indeed open) of FIG. 15A.

As shown at 1602, after the processing of FIG. 16, in this example, accessibility is separately checked through what may be characterized as a second stage of a two-stage comparator operation. Such processing might be performed by a suitable notification management processor. The second stage of the two-stage comparator operation, as characterized herein, is described below with reference to FIG. 17.

As described above, the processing in FIG. 16 of step 361(2), step 361(3), and step 361(4) shows processing in which cognitive related parameters are aggregated and/or mapped so as to allow the system to understand such cognitive related parameters. FIG. 17 is a diagram showing further details of cognitive window processing, in accordance with at least some embodiments of the invention. In the diagram in FIG. 17, and the processing illustratively described, cognitive parameters are mapped to determine if the user is cognitively aware and can possibly accept an upcoming notification or pending notification, etc. As reflected at 1701, the determination of whether a "cognitive window" is "open" means, in accord with one embodiment, a determination by the system of whether predetermined criteria are satisfied so as to "open" the cognitive window. If the predetermined criteria are not satisfied, then the processing will deem that the cognitive window is not open. On the other hand, if the predetermined criteria are satisfied, then the processing will deem that the cognitive window is open. The predetermined criteria might be in the form of a particular predetermined pattern. On the other hand, the predetermined criteria might be in the form of a particular threshold, sequence, threshold summation, or some other attribute of one or more data.

In the example of FIG. 17, the user's heart rate is elevated so as to indicate a particular stress level, such as via a particular "lookup" to heart rates. Further, data indicating the user's calendar is full of side-by-side meetings that would indicate her activity is busy. Further, the user is currently running—so she is also performing a task. As a result, illustrative processing may include:

Trigger the notification if the following conditions are met.

Heart Rate=Moderate (not sleeping)
AND
Busy=Moderate to Low (not too busy)
AND
Not currently performing a task (i.e. Running)
AND
There isn't a major storm (i.e. Hurricane)
AND
EEG shows individual is not depressed currently (mild improvement would be ok based on trending and situations)=User should accept notification presented
Otherwise, forward notification to someone else in the system such as a caregiver if too much time elapses or if the priority is high enough due to number of high priority queued triggers.

Accordingly, as shown at 1702, in the illustrative processing, the system maps the "cognitive parameters" to determine if the cognitive parameters reflect a scenario in which the user or caregiver can accept a notification. The cognitive parameters might be input data that relates to the cognitive situation of the user. Such mapping may include determining if the observed inputs, observed by the CAND system, correspond to particular criteria such as one or more of a pattern, satisfaction of a Boolean requirement, satisfaction of a particular weighting or sum of weights amongst particular inputs, and/or satisfaction of a particular threshold value or values amongst particular inputs, for example.

Figure 18:
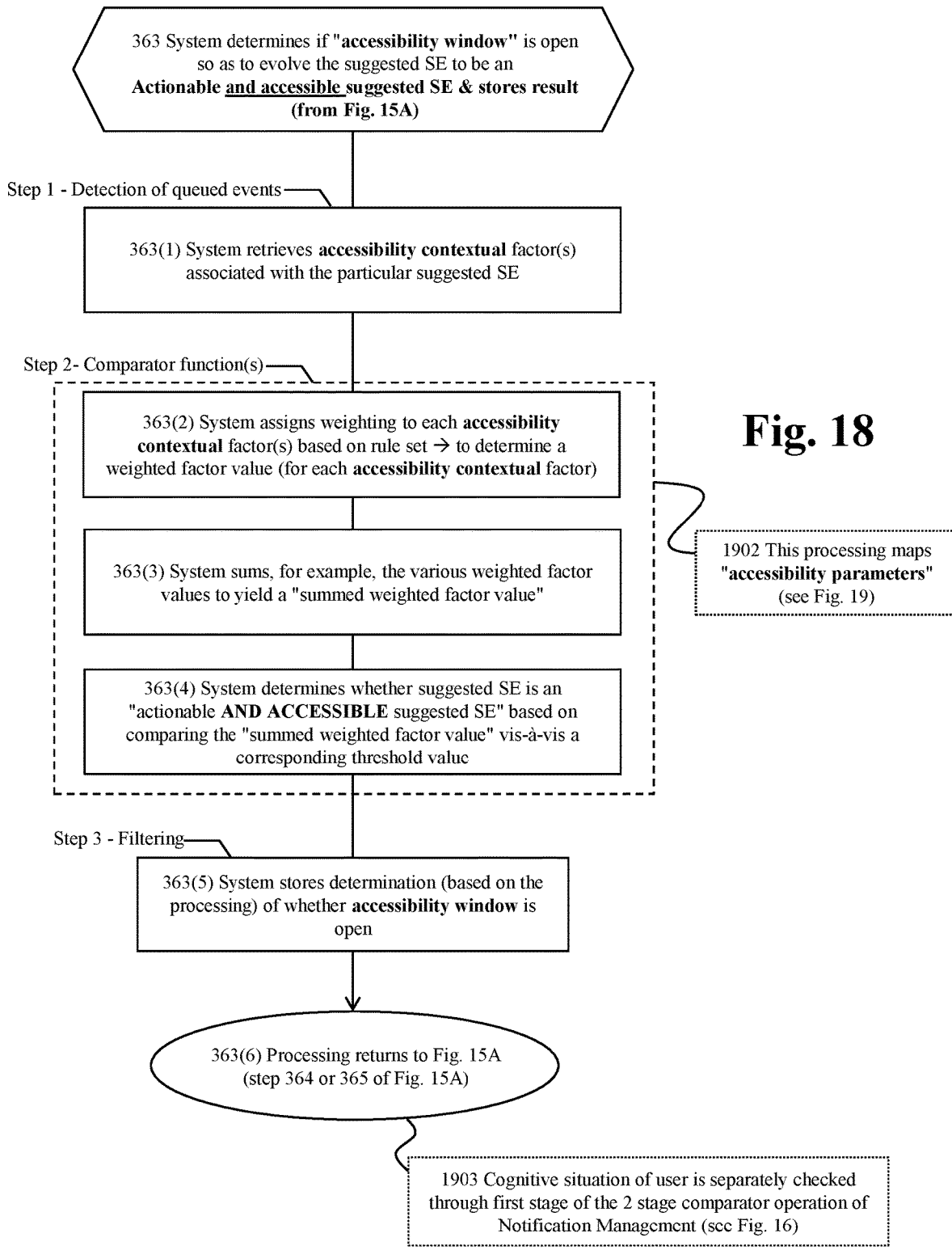
FIG. 18 is a flowchart showing further details of the system determines if accessibility window is open so as to evolve the suggested system event to be an accessible (and in this case actionable) suggested system event step of FIG. 15, accordance with at least one embodiment of the invention.

FIG. 18 is a flowchart showing further details of the system determines if accessibility window is open so as to evolve the suggested system event to be an accessible (and in this case actionable) suggested system event step 363 of FIG. 15, in accordance with at least one embodiment of the invention. Accordingly, in this example, the processing of FIG. 18 will yield (or not yield) a "perfected" system event. Note that such processing may only potentially yield a perfected system event since both the actionable window processing and the accessible window processing is illustrated as being performed.

As shown, processing of FIG. 18 starts in step 363 and passes to step 363(1). Step 363(1) may be characterized as a Step 1—detection of queued events. In step 363(1), the CAND system retrieves accessibility contextual factors associated with the particular suggested system event. Then, the process passes to step 363(2). In step 363(2), the system assigns weighting to each accessibility contextual factor based on a rule set—to determine a weighted factor value for each accessibility contextual factor. Then, the processing passes to step 363(3). In step 363(3), the system sums, for example, the various weighted factor values to yield a summed weighted factor value.

Then, in step 363(4), the system determines whether the suggested system event is an actionable AND ACCESSIBLE suggested system event based on comparing the summed weighted factor value vis-à-vis a corresponding threshold value, for example. After the processing of step 363(4), the process passes to step 363(5).

In step 363(5), the system stores the determination of the processing, i.e. the system stores the determination of whether the accessibility window is open or whether the accessibility window is not open. Step 363(5) may be characterized as a Step 3 filtering function. Then, the processing passes to step 363(6). In step 363(6), process returns to FIG. 15. Specifically, either the processing returns to step 364 of FIG. 15A (accessibility window not open) or the processing returns to step 365 of FIG. 15A (accessibility window is open).

As reflected at 1903, accordingly, the cognitive situation of the user is separately checked through a first stage of the two-stage comparator operation, which may be performed by a notification management processing portion, for example.

As reflected at 1902, the processing performed by steps 363(2), 363(3), 363(4) effectively "maps" accessibility parameters to known criteria. Details are described below with reference to FIG. 19. Collectively, the steps 363(2), 363(3), 363(4) may be characterized as a comparator function(s)—Step 2. FIG. 19 is a diagram showing in further detail the mapping of accessibility parameters, in accordance with at least one embodiment of the invention.

As shown, the processing maps "accessibility parameters" (i.e. input data that relates to the "accessibility" situation of user) to determine if the accessibility parameters reflect a scenario in which the user/caregiver can accept a notification. The accessibility parameters may be data input from sensors or other type of data. Such mapping may include, for example, determining if the observed inputs correspond to predetermined criteria: satisfaction of a particular pattern, satisfaction of a Boolean requirement, satisfaction of a particular weighting, satisfaction of a sum of weights amongst all inputs, satisfaction of a sum of weights amongst particular inputs, and/or satisfaction of particular threshold value or values, for example.

Various further features of the CAND system are described below.

Figure 20:
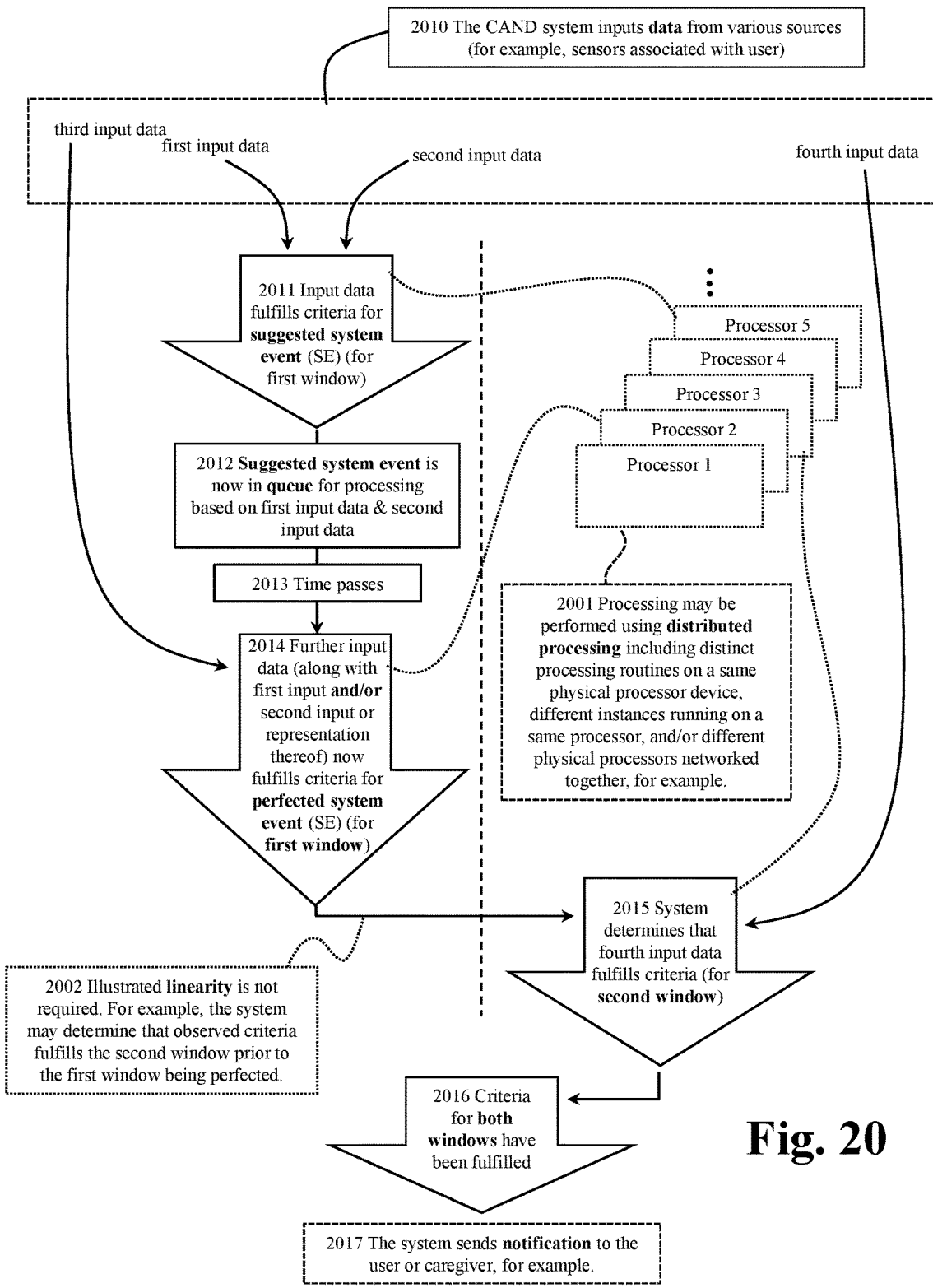
FIG. 20 provides a diagram showing various aspects of input data processing in accordance with at least one embodiment of the invention.

FIG. 20 is a diagram showing aspects of processing in accordance with at least one embodiment of the invention. As shown at 2010, the CAND system inputs data from various sources. For example, data may be input from sensors associated with the user, data input from backend databases and/or data input from a wide variety of other sources.

Such data, as illustrated in the example of FIG. 20, includes first input data and second input data. As shown at 2011, the first input data and the second input data are processed by the CAND system and determined to satisfy, i.e. fulfill, criteria for a "suggested system" event (SE) for a first window. For example, the first window might be a cognitive based window, as otherwise described herein. In other words, the first input data and the second input data are sufficient to create a "suggested" system event, but such observed data is not sufficient to create a "perfected" system event. In other words, the system knows that the first input data and the second input data are suggestive that a notification should ultimately be sent, in accordance with at least one embodiment of the invention. However, such first input data and second input data are not sufficient for the system to indeed send such notification. As reflected at 2012, (even though a notification is not sent) a "suggested" system event is now generated and put in queue, for processing, based on the first input data and the second input data. Then, as reflected at 2013 of FIG. 20, time passes by until further data is input.

That is, as shown at 2014, the system inputs further input data and processes such further data, along with the first input data and/or the second input data (or alternatively a representation of the first input data and/or the second input data as represented in the queued "suggested event"). The system determines that the further input data now indeed fulfills the criteria for a "perfected" system event for the first window. The perfection of the system event might have resulted from (1) a combination of the further input data along with the first input data; (2) a combination of the further input data along with the second input data; or (3) a combination of the first input data, the second input data, AND the further data.

As reflected at 2001, it is appreciated that the illustrated processing may be performed using distributed processing including distinct processing routines on a same physical processor device, different instances running on a same processor, and/or different physical processors networked together, for example. Such distributed system is reflected by the processor 1, processor 2, processor 3, and processor 4 of FIG. 20.

Additionally, as reflected at 2002, the linearity illustrated in FIG. 20 is not required. For example, the system may determine that observed criteria fulfills the second window prior to the first window being perfected. As a result, upon the first window being perfected, the system can immediately move to sending the particular notification. Such approach results in improved efficiency and speed. Accordingly, as reflected at 2016, criteria for both windows have been fulfilled. For example, the two windows can include a cognitive window (as noted above) and an accessibility window, for example.

Accordingly, at 2017, the system sends a notification to the particular user. For example, the recipient might be the user herself, or a caregiver of the user, for example.

A significant technical problem with notifications today is that they are highly inefficient. Notifications are sent to users indeterminately. Systems are structured to send notifications to users uncertain if the user will see or act upon the notification. Therefore, notifications are often sent more than once. Further, systems may have alternative notification options if the first option was unsuccessful leading to even more notifications being transmitted. These inefficient systems clog networks with multiple notifications, consume power of the network and devices, and consume bandwidth.

A technical advantage of the present invention is the ability to assess and improve the efficiency of the network by making improved notification decisions. Through the systems' ability to limit or minimize notifications to preferred or optimized times, devices, and notification channels the system improves the overall efficiency. Such improvements include limiting usage of power consumption of devices in the network and limiting bandwidth of the notification channels (telecom, Wi-Fi, internet, etc.).

The system is not only capable of identifying the devices in the network but can also identify or determine the available power and the power usage profiles of the devices. Such usage profile can be based on known profiles or by reading or monitoring the power consumption of the devices over time (short or extended). For example, the system can ping devices in the network and obtain power level data on the devices before and after a notification to determine power consumption. Further, the system can ping a device prior to a notification to determine the power level of the device to determine if it has enough power to receive the notification; or if the device is currently being charged. Through use of the data on the available power and the power consumption profile of the device, the system can identify devices in the network that are both available (or likely to be available when a notification is ready to be sent) and which are likely to use less power when receiving a notification(s). Therefore, the system can make analytical decisions on which devices are most efficient for receiving a notification. Such analysis or efficiency could be based on which devices consume less power, which devices are most likely to be seen (and the notification acted upon) by the user; and which devices are likely to be marginally impacted (i.e. device is charging, and battery power consumption would be offset).

The system can also identify and analyze available communication paths or notification channels for the various devices. The system can review the communication paths to each device which may include multiple paths or links which may be dependent or independent. For example, the paths might include telecommunication networks, internet, wide area networks, local area networks, Wi-Fi, and Bluetooth. The system can also factor into the analysis the reliability of each communication path and bandwidth, cost, and time of sending the alternative notification types (i.e. SMS text, mobile app notification, mobile device call, local hub notification through internet/WIFI). Such cost data could include analysis on a user's mobile phone plan (i.e. unlimited vs. limited, cost of bandwidth, allowable SMS messages), home network plan (internet service, free Wi-Fi), and other related network plans and costs. Further, the system can determine reliability of both the message being delivered (network reliability) and the message being acted upon (SMS vs. in-app notification).

Ultimately, the system through (one or more efficiency analysis processors) can identify the optimized time, type, and channel (or channels) for a notification based on the user being accessible, cognitively available and the power data analysis and network communication data analysis. The system therefore provides a technical solution of smart notifications based on improved delivery protocols as well as improved efficiencies on power consumption, network activity, and communication reliability and cost.

Figure 21:
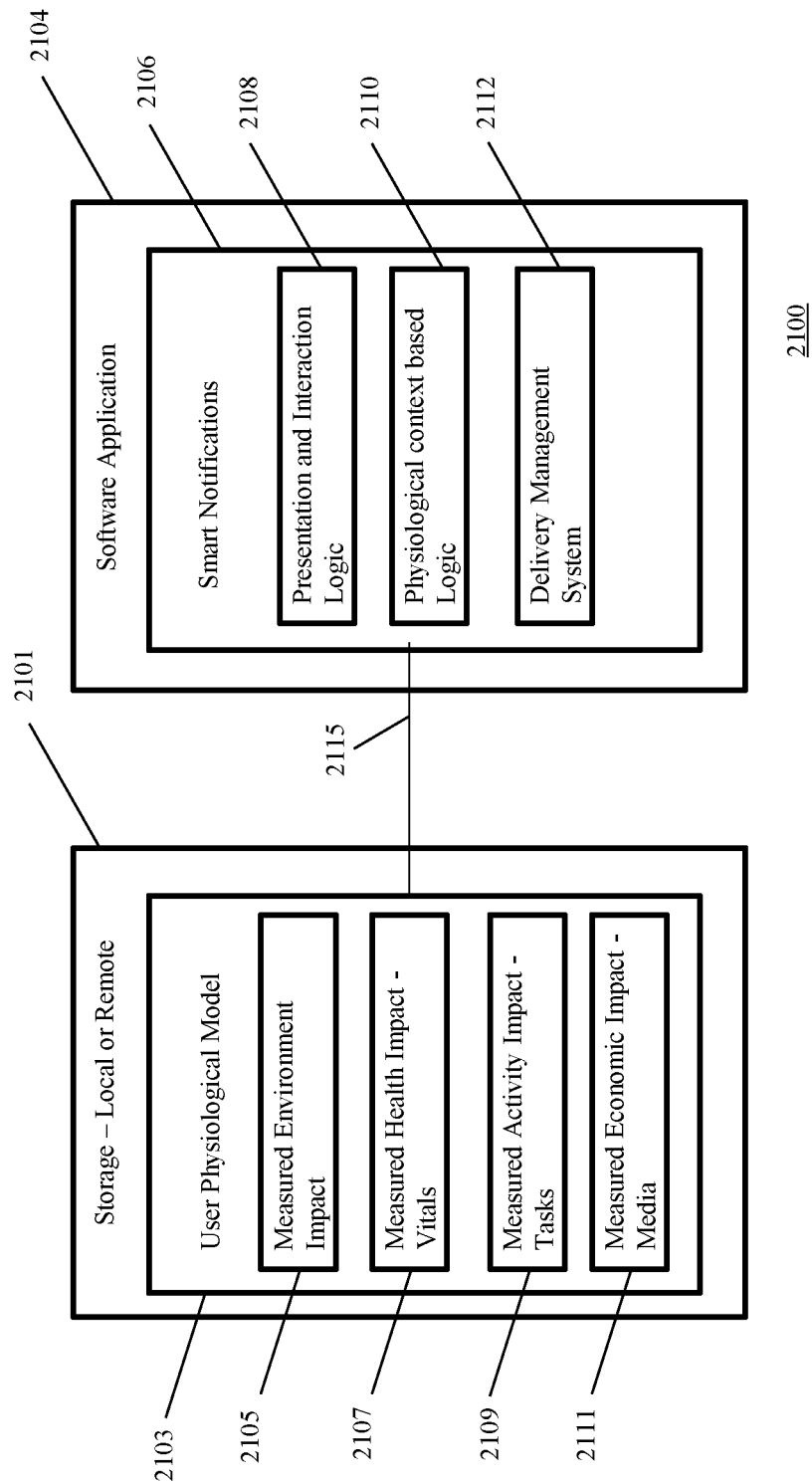
FIG. 21 is a system diagram, in accordance with at least one embodiment of the invention.

As depicted in FIG. 21, the present invention provides a notification system that analyzes the physiological state of the user to deliver notifications when the user is anticipated to be both cognitively receptive to and able to act on the receipt of the notification. The system 2100 includes a memory or Storage 2101. Within the memory or Storage 2101 resides a User Physiological Model 2103 for an individual user. The Storage 2101 for this User Physiological Model would reside either locally or remotely and can be real-time updated through a connected interface.

The User Physiological Model 2103 includes information from sensing elements such as: the Measured Environmental Impact 2105, the Measured Health and Physiological Impact 2107, the Measured Activity Impact 2109, and the Measured Economic Impact 2111.

The Measured Environmental Impact 2105 may include many sensing elements such as: weather sensors, sound sensors, particle sensors, gas sensors, light spectrum-heat detecting sensors, network analyzer sensors, radio communication analyzer sensors, magnetometer sensors, optical communication sensors, proximity detection sensors, position—movement sensors, and usage sensors. The weather sensors may use or sense light detection, temperature, atmospheric pressure (barometric), and capturing position of the sun and moon; sunrise and sun set; and local current weather measurement which can be augmented with regional, national, and global data. The sound sensors can be used to detect noise level, frequency identification, and transcriptive services to name a few. Particle sensors may be used to detect or measure dust particles and pollen level using particulate matter and low pulse occupancy (LPO), and smoke and mold spores by means of negative ion generator, or photoelectric light detection. Gas sensors may be used to detect gas or fumes which might have a detrimental (or positive) effect including: formaldehyde (Molecular Formula: $H_2CO$ or $CH_2O$); alcohol vapor (Molecular Formula: hydroxyl group-OH, e.g. Isopropyl-$C_3H_8O$ or $C_3H_7OH$ as well as Ethanol-$C_2H_6O$ or $C_2H_5OH$); benzene $(C_6H_6)$; Hexane $(C_6H_{14})$; Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CH$ $CH_3$ or $C_4H_{10}$ or $(CH$ $C_4H_{10})_2CHCH_3$); propane (Molecular Formula: $CH_3CH_2CH_3$ or $C_3H_8$); natural coal or town gas which could consist of methane or natural gas (Molecular Formula: $CH_4$); carbon dioxide (Molecular Formula: CO2); hydrogen (Molecular Formula: $H_2$); carbon monoxide or possibly smoke (Molecular Formula: CO); and oxygen (Molecular formula: $O_2$). Light spectrum-heat detecting sensors can be used to detect various environment aspects including: visual-light levels; movement; heat maps; light spectrum identification; infrared detection; UV radiation; and image recognition. Network analyzer sensors can be used to detect various network aspects including: available wireless networks; proximity; signal strength-RSSI; manufacturer information; serialization, addressing; standards-Wi-Fi, Bluetooth, Cellular; topology-MESH, Star, ring, point-to-point, bus, tree, hybrid; and network types (PAN, SAN, CAN, LAN, MAN, WAN, GAN). Radio communication analyzer sensors may be used to sense or detect: radio communication frequency; signal strength; active broadcasters; band (AM, FM, longwave, shortwave). Magnetometer sensors may be used to sense or detect: magnetic field-inductive sensing of polarity, multi-axis field strength detection, near-field communication (NFC). Optical communication sensors may be used to sense or detect: 3-dimensional positioning of sensing emitter, signal strength of emitter or emitters, and communication. Proximity detection sensors may be used to sense or detect radio signal strength feedbacks, light feedback, step responses, reactivity to nearby electro-magnetic objects and thermal heat placement to determine proximity of the user or devices. Position movement sensors may be used to detect or sense movement including: local position; altimeter-elevation; gravitational force; movement relative to a 3-axis accelerometer; degree of change; speed of change; and global positioning systems ("GPS" for determining global longitude, global latitude, global degree of change, global speed of change). The system may also employ usage sensors to detect usage such as electricity for individual appliances or outlets, and total electricity used, active outlets versus inactive outlets, garage door usage, open or closed doors, water leak detection, water usage, open or closed windows, car distance traveled, car operating or car off, garbage empty or garbage full, natural gas, LPG, petroleum gas, water return/waste, phone and internet usage.

The Measured Health and Physiological Impact (Vitals) 2107 may include many sensing elements such as: temperature sensors, heart rate sensors, pulse rate sensors, respiratory sensors, blood pressure sensors, metabolic sensors, circulatory sensors, neuro sensors, cardiac sensors, nerve sensors, pain response sensors, awake/sleep sensors, and health context sensors. Temperature sensors may be used to collect internal, surface level, and external temperature. Heart rate sensors may detect, or sense heart rate and heart signal characteristics based on the heartbeat and/or derived from an electrical impulse within the QRS signal. Pulse rate sensors may be used to detect, measure, or sense: the blood flowing through the circulatory system using a circulatory based sensor like Blood Pressure or a Pulse Oximeter; or collecting blood flow transit time rate in conjunction with a QRS signal or additional circulatory sensors (per location on the body). Respiratory sensors may be used to collect respiratory-breathing rate, positive airway pressure to the lungs, physiological signal of forced expiratory volume, and forced vital capacity. Blood pressure sensors may be used to measure and collect degree of stress, degree of arteries constricted (vasoconstriction), white coat syndrome, medication influenced, exercise influence, and resting state. Metabolic sensors may be used, including blood glucose sensors, to collect blood sugar levels, metabolism before/after meals, detoxification influences, and sleeping influences. Circulatory sensors may be used to detect or sense pulse oximetry as an indirect measure of oxygen saturation ($SpO_2$), a direct collection of arterial blood gases ($SaO_2$), partial pressure ($PaO_2$), tissue oxygen saturation ($StO_2$) and other $O_2$ data collection sites within the body, signal strength, and photoplethysmography (PPG). Neuro sensors may be used, including using EEG-brain sensors, to collect stress indicators, sleep indicators, and disorders. Cardiac sensors may be used, including using ECG, to collect heart activity, electrical impulses, QRS, and R-R interval. Nerve sensors may be used, including sensing the vagus nerve, and collecting resting state of the body's organs measured using vagal tone, and respiratory sinus arrhythmia (RSA). Pain response sensors may be used, including collecting salival level of cortisol, to determine pain and stress (measured for example using pain level combined with vagal tone, RSA, blood pressure and heart rate). Awake and sleep sensors may be used to collect, and measure awake and sleep data including the environmental impact (e.g. movement, audible indicators-snoring, teeth grinding, sleep talking) combined with vitals (e.g. EEG—providing cortex activity, NREM, REM, sleep depth; ECG-providing Heart rate changes; Respiration-changes, CPAP detection) and sweating (e.g. body temperature, perspiring and rate of perspiration). Health context sensors may be used to determine various health conditions including weight sensors, height through lift sensors and light detection, skin pigmentation and hair color through camera and light frequency detection, dry skin rating via electrical conductivity, dry tongue via electrical conductivity, eye dryness via camera data collection, hearing tests, and coughing via audio recording.

The Measured Activity Impact (Tasks) 2109 may include many sensing elements such as: food sensors, bathroom sensors, personal product sensors, shock sensors, daily task sensors, exercise sensors, travel sensors, appliance sensors, relaxation sensors, and hardware usage sensors. Food Sensors may include caloric sensors, gluten detection sensors, meal detection sensors to define, sense, or measure eating-nutrition, calories, meal status. Bathroom sensors may include using environmental usage sensor(s) of electricity, water and waste suggesting using the bathroom, toilet, or shower. Personal product sensors may sense or collect data on using a toothbrush sensor for brushing teeth, movement sensors connected to makeup or hairbrush for detecting combing hair, and feedback products like electrical stimulation for managing habitual needs (shock sensors). Daily task sensors may be used for sensing or collecting data on using a calendar, email activity, call activities suggesting working-busy day, light work day, planning to leave early/late, planning to arrive early/late, needing to focus-do not disturb; meetings-presenter, decision maker, note taker, passive listener; conversations-deeply engaged, or mildly listening; chores-mowing, auto services, home services, and personal services (purchases, healthcare checkups, dental checkups, physical and mental health-chiropractic, massages, acupuncture, therapist, community groups). Exercise sensors may be used to sense or collect data including equipment reporting-workout time, intensity, calories burned, energy level, and category including weights, cardio, and yoga. Travel sensors may sense or collect data from emails, travel applications, environment sensors detecting indirect traveling (i.e. someone else is doing the work), and direct traveling (i.e. driving, cycling, rowing, running). Appliance sensors may be used to detect or sense using fridges and ovens to describe level of cooking-status as engaged, lightly engaged, not engaged; or using the clothes washer, clothes dryer, dishwasher for chores detection along with increased water usage and electricity changes. Relaxation, meditation and sleep sensors may be used including EEG-based sensors, audio detection, motion detection, to determine various duration, status, depth, and suggestions. Hardware usage sensors may be used to passively collect data on usage of devices from sensors from mobile phones, portable audio devices, hands-free voice recognized playback and internet driven cognitive computing devices, televisions, tablets, e-readers, hubs and providing a collection of information on charging, battery level, screen usage, interactions-touch, buttons, frequency, patterns, number of apps, app classification, app usage, call log, email usage, SMS usage; and self-reported hobbies.

The Measured Economic Impact (Media) 2111 may include many sensing elements such as: news related sensors, work-life balance sensors, finance related sensors, and hospital or care related sensors. News related sensors may include web crawling and news media feeds for cognitive computing of news with reporting based on current location, surroundings or home, and friends' locations to define user recognizable personalized global tragic events, global heightened security, global impact level and national tragic events, national heightened security, and national impact level; local tragic events, local heightened security, and local impact level. Work-life balance sensors or data may be collected through calendar, globally available calendars, and suggested activities planned in relation to work-life balance, by measuring holiday-working and related stress; weekend-working and related stress; travel impact-cancellations, planned departure, delays, arrival times traffic-heavy traffic on route, crashes, police; and closures of an office or school. Finance related sensors or data may be collected through personal finance companies that the user provides access for assessing financial-gains, losses, stocks, investments, upcoming bills to pay, risks in due dates and running tight of funds for the month. The measured economic impact 2111 may also include hospital or care related sensors and data collected through media, calendars, emails from hospitals or care providers including data on hospitalization, births, deaths-importance, and impact level.

The sensing elements utilized by the system to determine or measure the Measured Environmental Impact 2105, the Measured Health and Physiological Impact 2107, the Measured Activity Impact 2109, and the Measured Economic Impact 2111 may be direct, indirect (including $3^{rd}$ party sensors), passive, or active sensing elements. In addition, many of the sensing elements can integrate with a feedback loop such as a manually derived feedback survey loop. Such feedback loop systems are well suited for use with activity tasks, heath related sensors and measurements, environmental sensors and measurements, and economic sensing elements and measurements.

The system 2100 also includes a Software Application 2104 that can read the User Physiological Model 2103. An interface for reading the User Physiological Model exists within the Software Application 2104. The Software Application includes a Smart Notifications 2106 module or component based on the User Physiological Model. The Smart Notification 2106 includes a Presentation and Interaction Logic 2108 component; a Physiological and Context Based Logic 2110 component; and a Delivery Management System 2112 component.

The Presentation and Interaction Logic (how information is presented to the user) considers both situational analysis and available systems and proximity. Situationally it considers: loud situation-defined as priority or intense; normal situation-operates as designed; soft situation-defined as discrete or quiet; suspended situation-snooze and revisit later; automatically dismiss situation-cancel situation; and transfer situation-move situation to another user or system. As for available systems and proximity (how the system reaches the user) the system considers various paths and channels including: mobile phone; home health hub; portable health hub; car radio/navigation system; PC; home phone; connected caregiver systems (EHR—Electronic Health Records); and connected friends and family systems (including co-workers).

The Physiological and Context Based Logic 2110 determines situations that invoke presentations and interaction logic. The Physiological and Context Based Logic 2110 component includes a situation algorithm that determines presentation and interaction logic and situation based on user physiological model and the signal from the delivery management system. The Physiological and Context Based Logic 2110 component also considers the signal relationship to the User Physiological Model 2103. This includes the relationship model showing what information is relevant based on data retrieved from sensors either directly or indirectly related to the user's physiology and impact of vitals, surrounding environmental elements, tasks, and media.

The Software Application 2104 also includes a Delivery Management System 2112. The Delivery Management System 2212 provides base rules for all alerts, notifications, and user signaling of message delivery mechanisms. The Delivery Management System 2112 provides signal name and signal rules for triggering a notification.

The signal rules may be periodic or episodic. The periodic rules are regular triggered events occurring on a timed interval and may include: an initial time of trigger such as time of day, time (e.g. number of seconds) from now, counter time from base time (where base time is referenced within the system as a counter with a reference to absolute 0 defined as start time), and time from start time; a reoccurrence time trigger such as every, every other, custom repeating pattern of enabled versus disabled (e.g. first 3 are on and next 3 are off), multi-combination (e.g. pattern 1=custom, where first 3 on, fourth is off, then pattern 2=every; an interval rate trigger such as time between occurrence with units and reference, where units can be a unit of time or a count value, and reference defines the unit; and exceptions such as occurrences that have been excluded, specified as count values, time and date, or number of occurrences to silence until next occurrence. The episodic rules are triggered events occurring on a rule-based pattern. The rule based pattern may be based on rule monitoring such as defined with WHEN, IF, AND/OR, THEN, AND THEN. Where WHEN determines initial rule trigger, IF determines the next trigger or triggers, AND/OR defines logic within the trigger and THEN describes the action. This may be based on information from the user physiological model and is directly or indirectly related to the user's physiology and impact of vitals, surrounding environmental elements, tasks, and media. The rule based pattern may also be action based such as starting the notification on a periodic basis with or based on settings as described within the periodic rule and when to stop periodic notification.

Personalized Notification Behavior UX/UI:

The system 2100 collects various data elements from numerous devices in the network including the following data: user requests; user behaviors and patterns; and sensor data. User requests include how the user interacts with the system by enabling sources of data and accepting or rejecting notifications delivered to the user. User behaviors and patterns includes behaviors and patterns which may be defined by the user during first time or early use including identification of their preferences. The system 2100 may ask them to define their approximate sleep times, work times, enable calendar objects to be shared, sensor data, delivery preferences and friends and family. Additionally, this information may be supplemented by machine learning where actions are recorded and, based on advanced configurations available to the user, can automatically be applied to learn over their preferences or availability time (e.g. if the user regularly dismisses a notification, they could be asked to see less of the dismissed notifications, and then give a reason as to why). The reason can then be applied across similar notifications in the future as it learns the user's preferences real-time. Further, the system 2100 collections sensor data which can be captured passively and directly from sensors on the hardware(s) or devices that are running the application(s) for the system 2100. The collection of sensor data may be active, continuous, or periodic and directly (or indirectly) from sensors both inside and outside of the hardware(s) or devices that are available to the user and/or which have been permitted by the user.

During daily use, the user may receive tailored notifications and alerts, soft tasks, and status notifications. The tailored notifications and alerts are the notifications that are delivered in a manner corresponding to how the user would like to be notified in the given situation. Soft tasks are notifications that are planned and are silently updated giving the user the knowledge of what may occur next and what is required for it to occur. Status information are a list of what notifications and alerts have been delivered, which systems they were delivered to, which users they were delivered to, and if they were not delivered the reason they were not delivered (or acted upon.

The system 2100 also determines which channel and device to deliver the notification. The channel selected for notification could be one of the following: (1) local wearable system, where delivery occurs through a wearable system for instance: a watch, a patch, a strap or band, a clothing item or accessory embedded with technology capable of communicating, and delivery notifications; (2) local portable system, where delivery occurs through a computer that the user can carry with them, for instance: a mobile phone, a tablet, a laptop or some combination of these. (This would also support a hub which may or may not have a user interface for interacting but would not be solely relying on a stationary power source); (3) local stationary system, where delivery occurs through a location stationary device that requires stationary power source (the system could either have a user interface or not require a user interface); and (4) remote system, where delivery occurs through the existing user or another user's equipment that may include a wearable system, portable system, or stationary system. The interfaces for the location stationary system could include a television, a set top box using a digital or analog connection to a television, a gaming console, a home audio system, a phone system, appliances, a navigation system in a car, or a clock.

The system 2100 can also determine or has rules, which identify, based on certain situations, when a user is not notified. These instances might include where the user is unable to perform the requested action, where the user is disrupted and unable to perform the requested action, or where the situation is not appropriate. For example, the user may not be at the location to take action (e.g. a weight scale sensor is at home and the user is at work), or the equipment is not with the user (e.g. a medication monitor was forgotten in the car). This may cause the system 2100 to postponed notification, and may generate a different notification. Instead of "time to take your medication", the system reports earlier to the user "please make sure you have your medication as you will need in 8 hours" when the user leaves the medication behind and it assumes they are going to work based on user preferences or user learned behavior. In such an instance, the user can also indicate to the system if they would like to see more notifications or alerts like these, and if not, they can give a reason such as "only notify me if the reminder is due in 4 hours", which may be because the user usually goes to lunch and has their medication outside of the office. Further, an example of a non-delivery notification may occur when the disruption of the notification is not appropriate such as when the system identifies the user may be driving (e.g. speed of the user in relation to their surroundings suggests they are in a car and cannot take their blood pressure reading, and to avoid).

In some instances, the system may determine that notification delivery may distribute to one or more of the following: directly to the devices or hardware(s) that the application(s) are running on in the system; and directly to the devices or hardware(s) that the application has been permitted to communicate with from the user.

Figure 22:
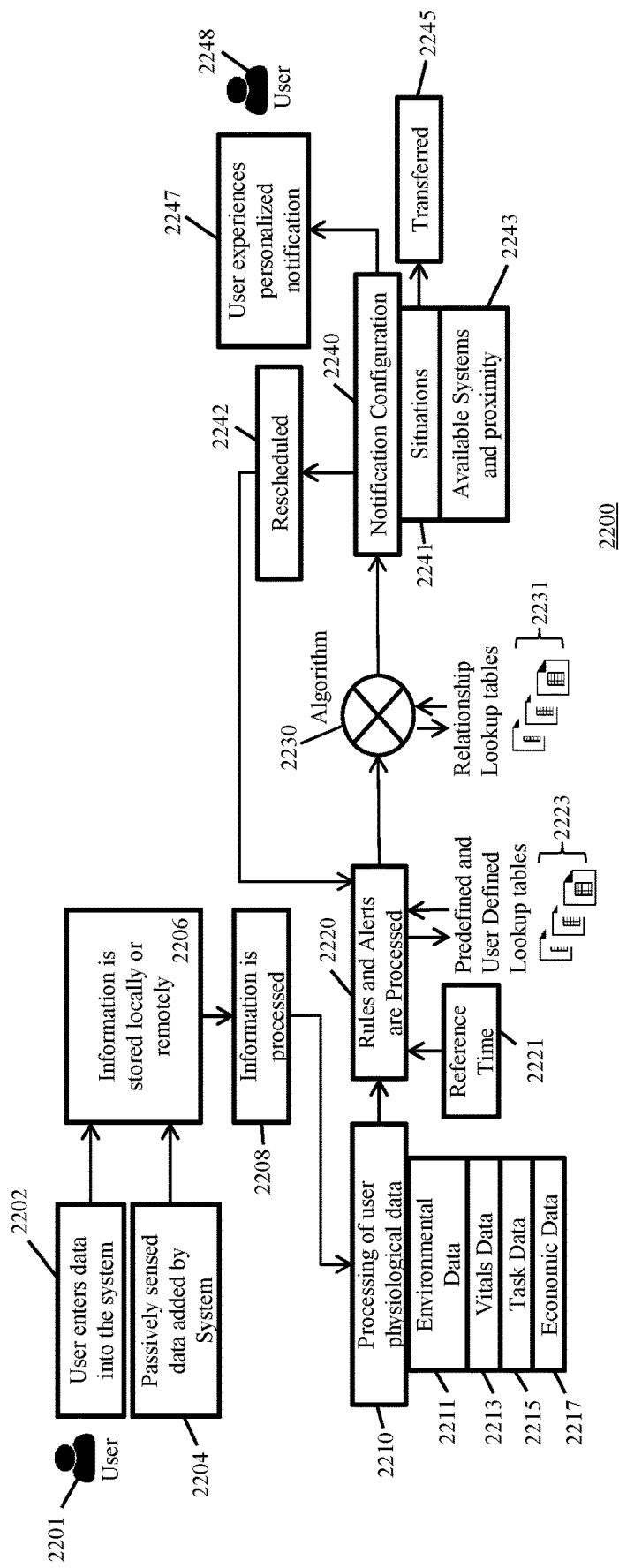
FIG. 22 provides an illustration of information or logic flow, in accordance with at least one embodiment of the invention.

FIG. 22 provides an illustration of the information or logic flow 2200 of the notification system of the present invention. The system may employ various logic, rules, and algorithms using relationship lookup tables between user physiological data and varying situations is able to determine the appropriate notification behavior for personalized configuration and delivery analysis. A user 2201 may actively enter data into the system in step 2202. The user entered data may include basic or personal information as well as preferences. In addition, in step 2204, the system tracks and adds passively sensed data. Such data may be through various network devices and sensors or from external devices or sensors. The system stores data, step 2206, both locally and remotely. The system then processes the information in step 2208. Part of the processing of information includes the processing of user physiological data (step 2210). The physiological data includes environmental data 2211, vitals data 2213, task data 2215, and economic data 2217.

The system also processes one or more rules and/or alerts in step 220. The rules and alerts are based on a reference time 2221 and the predefined and user defined lookup tables 2223. Further, the rules and alerts also help to refine the lookup tables 2223. The rules and alerts 2220 are also processed against one or more analytical processes or algorithms 2230 which may use one or more relationship tables 2231. The system, using the various data, rules and alerts, and analysis then analyzes the notifications configurations 2240. The notification configuration 2240 considers situations or situational data 2241 and available systems and proximity 2243. Available systems include analysis of the various devices in the system network. Available systems or devices include the devices in the home, office, and those of family, friends, and coworkers. If the system determines it is not the right time to send a notification, the notification is rescheduled in step 2242. The rescheduled notification would be processed again by the rules 2220, algorithms 2230 and notification configuration 2240 analysis.

Once the system determines all elements are present to presenting the notification, the system then presents a personalized notification to the user 2247. If the system determines the user needs a notification but the user is not available, the system can transfer the notification (step 2245) to a network device which may be the device of a family member, friend, or co-worker, or emergency personnel.

As previously discussed in conjunction with FIG. 1, there are several use case and scenario based environments that may impact the user's behavior and overall reception to informational queues or notifications. The environment or scenarios include: aspects related to the individual user's self or body; the user's local environment; the user's environment during a transition, travel, or exchange; and the user's environment in a remote situation such as at the office for work.

The self-environment includes scenarios that cover the individual, including the impact of daytime and nighttime, weather, environmental, eating and activity (caloric balance, calories in versus calories out), stress (brain activity), bathroom usage and hydration, physical state (such as weight, BMI) and well-being (such as Breathing Rate, Breathing Capacity, Oxygen transference to the Blood (SpO2), Heart Rate and QRS complex (Electrocardiogram), Arterial pulsatile wave shape (plethysmograph), and arterial pressure (blood pressure).

The local environment includes scenarios which cover the user in any local environment such as being at Home. The expectation of such environment might be that it is more calming due to proximity of friends and family, hobbies and improvement activities for home, others leading to the care of oneself. This includes activities like sleeping, exercising, chores, and overall quality of the environment.

The transition or exchange environment includes scenarios which cover the user while moving in between local and remote environments. The expectation of such environment is that it is a transitional state for the user where awareness is raised to nearby individuals and privacy walls are more conscience than while in a local environment. The transition environment includes transportation options like walking (running), flying, boating (cruises), bicycling (motorbike), and driving (public bus, taxi or private car). Each of these has different pickup locations, drop-off, and considerations with nearby passengers either within or externally present.

The remote environment includes scenarios which cover the user while in any remote environment such as an office. The expectation of such environment is that it may be of high stress due to the proximity of tasks and complexities bestowed on the user. A user that is shopping, or at a restaurant, or in an office will behave differently and respond to informational queues differently than when at home in a local environment.

Figure 23:
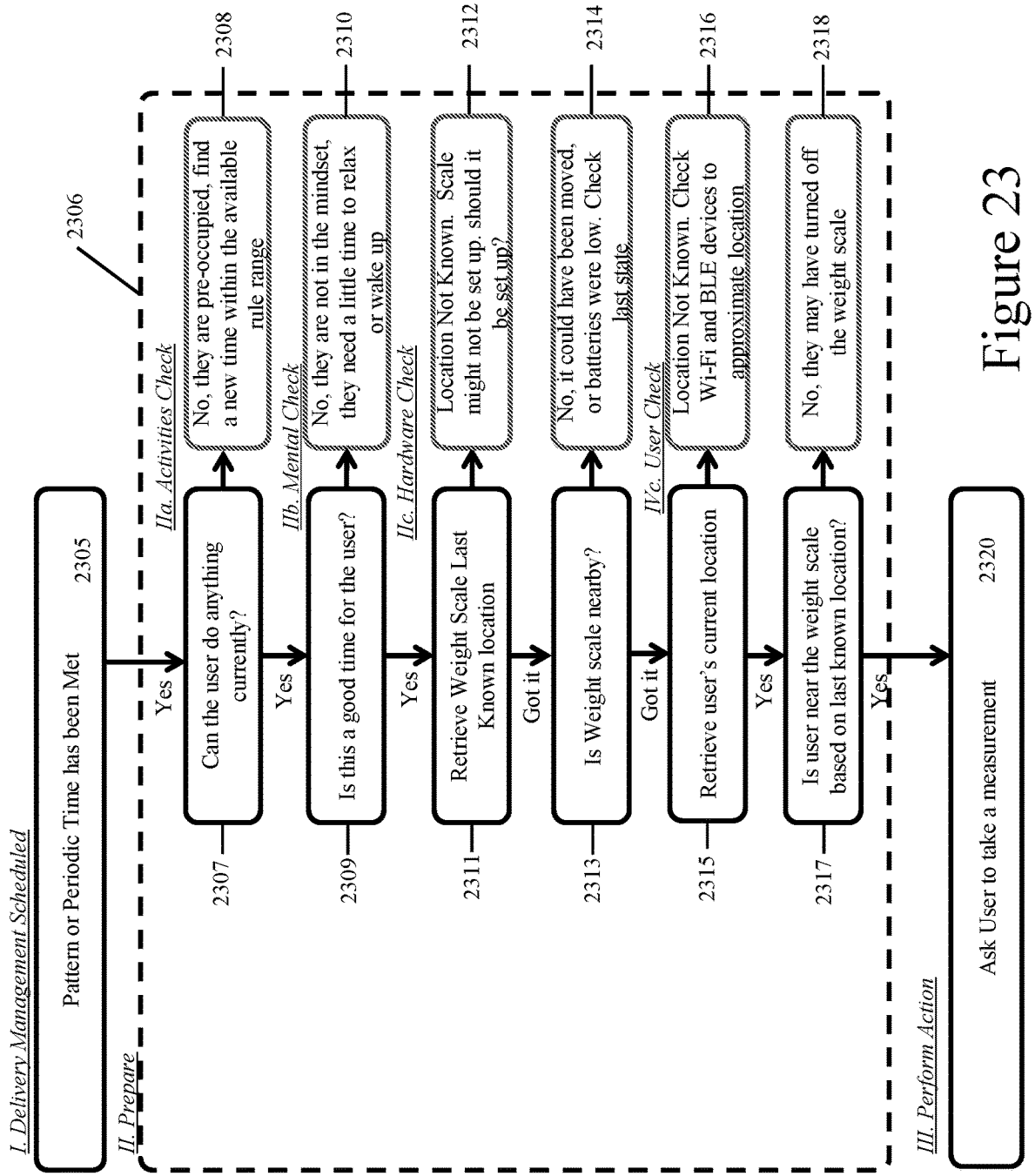
FIG. 23 provides a logic flow illustration in a scenario where the user cannot do anything about (act upon) the notification and it should be delayed until the user can, in accordance with at least one embodiment of the invention.

FIG. 23 provides a logic flow illustration 2300 in a scenario where the user cannot do anything about (act upon) the notification and it should be delayed until they can. An example is where the system wants to obtain the user's weight, but the weight scale is at home and user is not at home. The system, in step 2305 has identified that it wants to send a notification to remind the user to provide his weight. Such may be from user input or from stepping on a weight scale device which is part of or connected to the network. The system, then prepares to send the notification by analyzing various elements within the logic analysis 2306. In step 2307 the system performs an activity check and contemplates if the user is currently able to perform the task. In step 2308 the system determines the user is pre-occupied and must identify a new time within the rule range. Alternatively, if the system determines the user is capable of performing the task in step 2307, the system then performs a mental check (step 2309). If the user is not mentally ready (step 2310) then the system adjusts the timing of the notification. If the user is ready based on the mental check, the system (step 2311) proceeds to perform a device or hardware check or analysis. The system determines information on the last known location of the device and any last or recent data. If the system determines, in Step 2312, that the device is not ready the system may prompt for initiation of the device. Alternatively, if the device is ready, the system then determines if the device is in the same or same general location (step 2313). If the device is not in the same location (step 2314), the system may scan the network and attempt to identify the new location or other possible determination as to why the device is not available. If, in step 2313, the device is available and in the expected location, the system performs a user check. In step 2315 the system attempts to determine the user's current location. If the user's location is not known, the system (step 2316) may try to approximate the location based on various sensor and network data. If the user is determined to be near the weight scale, based on last known location, the system will transmit the notification asking the user (step 2320) to perform the task of measuring their weight. If the user does not respond to the notification, the system in step 2318 may attempt to identify the reasons such as the user has turned off the scale or ignored the notification.

Figure 24:
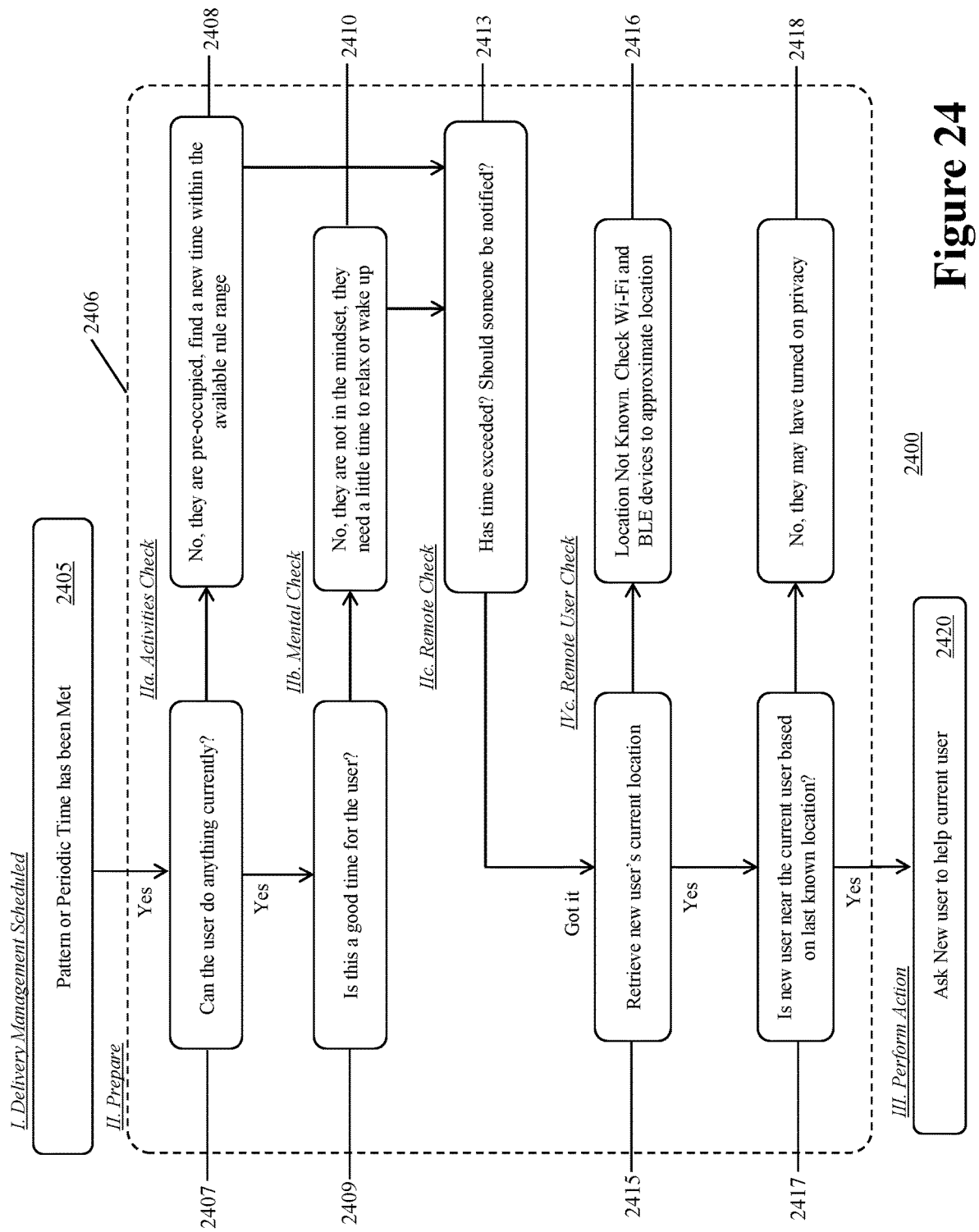
FIG. 24 provides a logic illustration in a scenario where the user is not able to respond or act upon the notification, but another individual may be able to assist, in accordance with at least one embodiment of the invention.

FIG. 24 provides a logic flow illustration 2400 in a scenario where the user is not able to respond or act upon the notification, but another individual may be able to assist. For example, sensor data might indicate the user is in a state of stress or pre-occupied and engage another person to interact with the user. The system, in step 2405 has identified that it wants to send a notification to the user. The system, then prepares to send the notification by analyzing various elements within the logic analysis 2406. In step 2407 the system performs an activity check and contemplates if the user is currently able to perform the task. In step 2408 the system determines the user is pre-occupied and must identify a new time within the rule range. Alternatively, if the system determines the user is capable of performing the task in step 2407, the system then performs a mental check (step 2409). If the user is not mentally ready (step 2410) then the system may adjust the timing of the notification.

However, the system may perform a remote check, for example, if the time has been exceeded (step 2413). The system is also capable of by passing step 2409 and 2410 and going from step 2408 directly to step 2413 if it determines conditions exists which warrant expedited notification (i.e. due to sensor data indicating a heightened status). If a remote check 2413 is needed, the system then seeks to retrieve a new user's (second person) current location. If the system cannot identify the location or the location is not known, step 2416, the system may attempt to approximate location based on various sensor and network data. If the new or second user is determined (step 2417) to be near the first user, then a notification is sent to the new or second user (step 2420). If the user does not respond to the notification, the system in step 2418 may attempt to identify alternative users and/or the reasons such second user has not responded or ignored the notification.

The system is also capable of adjusting or providing moderated notification levels including: loud, softer, or vibrate. The system can adjust the level based on the status of the user. For example, the system might send a loud notification is the user is sleeping. The system might send a soft notification if the system believes the user is not sleeping; and might send a vibration notification is the user is potentially occupied (i.e. at work).

High-Level Architecture Interfaces

Figure 25:
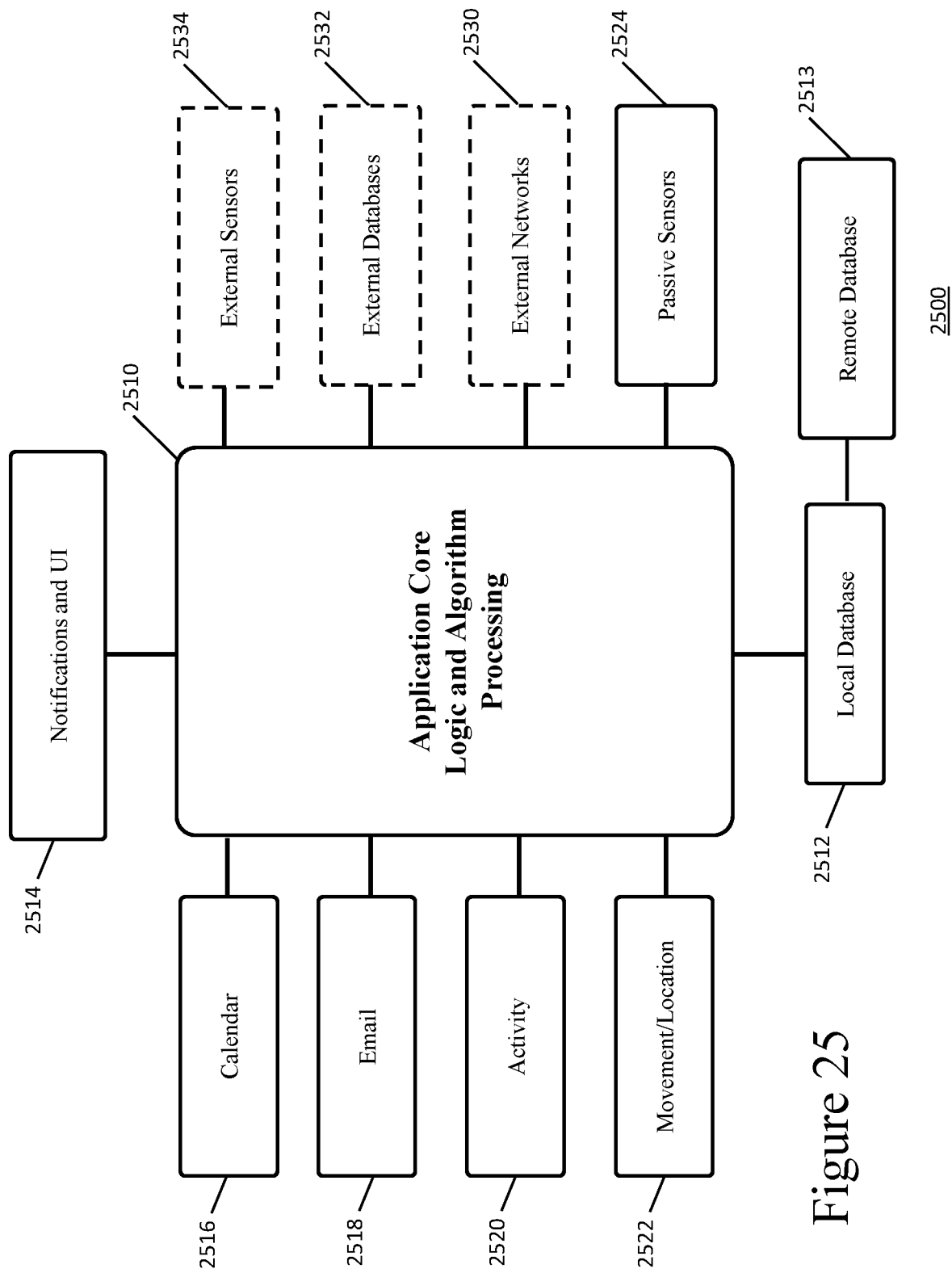

FIG. 25 provides an illustration of a high-level system architecture interface of the present invention. The system 2500 includes an application core logic and algorithm processing component 2510 which communicates with several interfaces, including local interfaces for calendar 2516, email 2518, activity 2520, movement/location 2522, passive sensors 2524, notifications/UI 2514, and a local database 2512. The local database 2512 can interact with a remote database 2516 that could be on the same hardware, network or a remote network as a backup or a synchronization point for the application to synchronize between other installations for the purpose of sharing and offloading of information. The system 2500 also interacts with external networks 2530, external databases 2532, and external sensors 2534.

Core Processing Classes

In an exemplary embodiment, the core processing classes of the system are broken up into 4 categories: (I) is the high-level interactions with the user which include the definition of the requests, the consumption of sensory information, and the presentation of the messaging; (II) is the management of the signaling for the periodic and episodic request generation; (III) is the management of the user's physiology including activities, environment, health and economy; and (IV) is the delivery management of the notification, and the situation modeling of the relationship to the user's physiology.

In one exemplary embodiment, there are several user roles that information is collected on or distributed to: (1) the administrator; (2) the user role; and (3) the friends, family, coworker role. The administrator role interacts by interacting with requests and the request class of the system. This forms the basis for the signaling that will drive the notifications ultimately. The default is determined to be set by the user acting as an administrator, with downstream changes occurring from administrators of systems outside of this interface. The requests then get triggered by the signal management describe in (II). The request provides information whether the request was triggered (an event generated by the signal manager) and whether it is meaningful (which is based on the rules defined within the signal itself to establish a temporary relationship with the physiology of the user.

The user role interacts with the request class, user class and message class by contributing information about themselves, their delivery systems, or the environment around them based on physiological sensors. The system will detect from user if they are able to respond based on activities and availability, and whether they are in a coherent cognitive state receptive to stimuli. Once determining if the request was triggered, if the request is meaningful, if the user is ready, if the user can respond and are coherent, then based on the situation the appropriate message and delivery needs are met, it is sent in a customized configuration to the end user in a means that is most receptive.

The friends and family role interacts with the message class to receive information based on the situation when a transfer of information is requested on behalf of the user. The system will notify an adjacent user of the system, classified as friends and family of the current user, the desired messaging that is most appropriate of the situation.

Signaling management happens when new signals are programmed into the system and are triggered based on periodic and episodic conditions. There may be more than one signal occurring at a time, or only a single signal. If there are more than one that the system may have additional prioritization that can be linked into this database for additional selection properties. The signals can be cleared if they are reset, or deleted if they are dismissed. Signals can also be updated to managed exceptions of occurrences within the system as to when the previous signal was cleared to better prioritize this for future occurrences. E.g. User dismisses event and an hour later if the same pattern exists, through machine learning the next event could be automatically dismissed. If a threshold or exception occurs, then there is the ability to force without exception.

Signals have patterns and sequences that describe their structure and duty cycle between active signals. Patterns may include multiple active signals then a timeout period, alternating sequences and regular timed occurrences.

The rules define the behavior relationship to the physiology of the user. For example, if the user is awake, and not stressed out, and is not driving, but in proximity of the weigh scale; then remind them to take a measurement. This may transition to the notification (IV) where a specific scenario is also selected for customized delivery to the user. (III) The physiology management happens whenever new sensory data, through passive or active requests occurs throughout the system. This could happen on a backend server where the data is collected from other servers and then populated in the database which is synchronized with the local database that the user is managing through active use of the delivery system.

The data is then collecting in separate buckets, including an activities database bucket, an environment database bucket, a health database bucket, and an economy database bucket. Each of these have utilities which allow the varying managers within the system to easily assess the current status of the user including, tasks, sun relationship, weather, air quality, pollution, positioning of the body in reference to the local and global systems and directional in an up or down or flat or standing position; stress, pain, satiety, relaxation, sleeping state, and overall impact of external events on the user's coherence.

For Activity, this includes varying tasks that make up a user's day, the time spent or planned time to spend, any roles that suggest the level of cognitive drain from the user and any effects that may contribute to other physiological areas.

For Environment, this includes varying sensors capable of measuring data within a stationary environment such as a home or office, or while the user is moving between stationary environments. Sensors may be collected from local systems, portable systems, or remote systems capable of collecting relevant location based data like weather systems.

For Health, this includes varying wearable sensors either on the body of the user, or that the user can directly interact with. These may be portable sensors that the individual can carry with them, or stationary sensors like weight scales which may be positioned in a bathroom.

For Economy, this includes external stimuli that may further impact the behavior and acceptance of new stimuli. This collected from calendars and news sources for the latest in global, national, and local occurrences.

Each of these physiological data points is captured in a way that allows for separation of concerns from a regulatory, security and user privacy perspective. The delivery management occurs through a series of interactions between delivery system utilities and situation utilities. A given delivery system must be identified based on the appropriate delivery mechanism. This is defined by the situation and the relationship to the physiology of the user.

Delivery types can include a mobile phone as well as other registered systems such as Hubs that can be used to passively monitor home environment or other stationary environments like an office, or a car system, or desktop, laptop, home phone, alternate phone, a caregiver system or a friends and family registered user system.

Situation Utilities define a Go/No-Go where the correct situation is identified, and lookup has been matched based on rules of the originating signal (I) and physiology (II) and mapped to the relationship model and database of the system.

It is appreciated that features of one embodiment as describe herein may be used in conjunction with one or more other embodiments.

The systems and methods of the invention in described embodiments may be implemented as a system, method, apparatus or article of manufacture using programming and/or engineering techniques related to software, firmware, hardware, or any combination thereof. The described operations may be implemented as code maintained in a "computer readable medium", where a processor may read and execute the code from the computer readable medium. A computer readable medium may comprise media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. The code implementing the described operations may be further implemented in hardware logic (e.g., an integrated circuit chip, Programmable Gate Array (PGA), Application Specific Integrated Circuit (ASIC), etc.). Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a computer readable medium at the receiving and transmitting stations or devices. An "article of manufacture" comprises computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the present invention, and that the article of manufacture may comprise suitable information bearing medium known in the art.

In an embodiment of the invention, the systems and methods use networks, wherein, the term, 'networks' means a system allowing interaction between two or more electronic devices, and includes any form of inter/intra enterprise environment such as the world wide web, Local Area Network (LAN), Wide Area Network (WAN), Storage Area Network (SAN) or any form of Intranet.

In an embodiment of the invention, the systems and methods can be practiced using any electronic device. An electronic device for the purpose of this invention is selected from any device capable of processing or representing data to a user and providing access to a network or any system similar to the internet, wherein the electronic device may be selected from but not limited to, personal computers, mobile phones, laptops, palmtops, tablets, portable media players and personal digital assistants.

As noted above, the processing machine used to implement the invention may be a suitable computer or other processing machine. The processing machine may also utilize (or be in the form of) any of a wide variety of other technologies including a special purpose computer, a computer system including a microcomputer, mini-computer or mainframe for example, a programmed microprocessor, a micro-controller, a peripheral integrated circuit element, a CSIC (Consumer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing the steps of the processes of the invention.

The processing machine used to implement the invention may utilize a suitable operating system (OS). Thus, embodiments of the invention may include a processing machine running the Unix operating system, the Apple iOS operating system, the Linux operating system, the Xenix operating system, the IBM AIX™ operating system, the Hewlett-Packard UX™ operating system, the Novell Netware™ operating system, the Sun Microsystems Solaris™ operating system, the OS/2™ operating system, the BeOS™ operating system, the Macintosh operating system (such as macOS™), the Apache operating system, an OpenStep™ operating system, the Android™ operating system (and variations distributed by Samsung, HTC, Huawei, LG, Motorola, Google, Blackberry, among others), the Windows 10™ operating system, the Windows Phone operating system, the Windows 8™ operating system, Microsoft Windows™ Vista™ operating system, the Microsoft Windows™ XP™ operating system, the Microsoft Windows™ NT™ operating system, the Windows™ 2000 operating system, or another operating system or platform.

The systems and methods of the invention may utilize non-operating systems (aka serverless architecture) as well for distributed processing. In the processing of the invention, services on cloud computing networks leveraging systems like AWS (as offered by Amazon Web Services, Inc.), BlueMix (as offered by IBM), and Microsoft Azure, can perform data collection services using varying technologies that are spun up on demand using tools like Chef to create container based deployments like Docker, or non-container compute services (e.g. AWS Lambda).

The invention provides real-time analytics processing that requires scale on demand to the users in the system, in accordance with at least one embodiment of the invention. Such offerings as AWS lambda and Kinesis (as offered by Amazon Web Services, Inc.) are among those that may be used in implementation of the invention. For example, AWS Lambda may be utilized to execute code (to perform processes of the invention) in response to various triggers including data changes, shifts in system state, or particular action taken by users. Similarly, in an embodiment, the OS (operating system) of the invention might be encapsulated in an EC2 instance (as offered by Amazon Web Services, Inc.) or multiple instances for deployment.

It is appreciated that in order to practice the method of the invention as described above, it is not necessary that the processors and/or the memories of the processing machine be physically located in the same geographical place. That is, each of the processors and the memories used by the processing machine may be located in geographically distinct locations and connected so as to communicate in any suitable manner, such as over a network of over multiple networks. Additionally, it is appreciated that each of the processor and/or the memory may be composed of different physical pieces of equipment. Accordingly, it is not necessary that the processor be one single piece of equipment in one location and that the memory be another single piece of equipment in another location. That is, it is contemplated that the processor may be two pieces of equipment in two different physical locations. The two distinct pieces of equipment may be connected in any suitable manner. Additionally, the memory may include two or more portions of memory in two or more physical locations.

To explain further, processing as described above is performed by various components and various memories. However, it is appreciated that the processing performed by two distinct components as described above may, in accordance with a further embodiment of the invention, be performed by a single component. Further, the processing performed by one distinct component as described above may be performed by two distinct components. In a similar manner, the memory storage performed by two distinct memory portions as described above may, in accordance with a further embodiment of the invention, be performed by a single memory portion. Further, the memory storage performed by one distinct memory portion as described above may be performed by two memory portions.

Further, as also described above, various technologies may be used to provide communication between the various processors and/or memories, as well as to allow the processors and/or the memories of the invention to communicate with any other entity; i.e., so as to obtain further instructions or to access and use remote memory stores, for example. Such technologies used to provide such communication might include a network, the Internet, Intranet, Extranet, LAN, an Ethernet, or any client server system that provides communication, for example. Such communications technologies may use any suitable protocol such as TCP/IP, UDP, or OSI, for example.

Further, multiple applications may be utilized to perform the various processing of the invention. Such multiple applications may be on the same network or adjacent networks, and split between non-cloud hardware, including local (on-premises) computing systems, and cloud computing resources, for example. Further, the systems and methods of the invention may use IPC (interprocess communication) style communication for module level communication. Various known IPC mechanisms may be utilized in the processing of the invention including, for example, shared memory (in which processes are provided access to the same memory block in conjunction with creating a buffer, which is shared, for the processes to communicate with each other), data records accessible by multiple processes at one time, and message passing (that allows applications to communicate using message queues).

As described above, a set of instructions is used in the processing of the invention. The set of instructions may be in the form of a program or software. The software may be in the form of system software or application software, for example. The software might also be in the form of a collection of separate programs, a program module within a larger program, or a portion of a program module, for example. The software used might also include modular programming in the form of object oriented programming. The software tells the processing machine what to do with the data being processed.

Further, it is appreciated that the instructions or set of instructions used in the implementation and operation of the invention may be in a suitable form such that the processing machine may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processing machine, i.e., to a particular type of computer, for example. The computer understands the machine language.

Any suitable programming language may be used in accordance with the various embodiments of the invention. Illustratively, the programming language used may include assembly language, Ada, APL, Basic, C, C++, C #, Objective C, COBOL, dBase, Forth, Fortran, Java, Modula-2, Node.JS, Pascal, Prolog, Python, REXX, Visual Basic, and/or JavaScript, for example. Further, it is not necessary that a single type of instructions or single programming language be utilized in conjunction with the operation of the system and method of the invention. Rather, any number of different programming languages may be utilized as is necessary or desirable.

Also, the instructions and/or data used in the practice of the invention may utilize any compression or encryption technique or algorithm, as may be desired. An encryption module might be used to encrypt data. Further, files or other data may be decrypted using a suitable decryption module, for example.

As described above, the invention may illustratively be embodied in the form of a processing machine, including a computer or computer system, for example, that includes at least one memory. It is to be appreciated that the set of instructions, i.e., the software for example, that enables the computer operating system to perform the operations described above may be contained on any of a wide variety of media or medium, as desired. Further, the data that is processed by the set of instructions might also be contained on any of a wide variety of media or medium. That is, the particular medium, i.e., the memory in the processing machine, utilized to hold the set of instructions and/or the data used in the invention may take on any of a variety of physical forms or transmissions, for example. Illustratively, as also described above, the medium may be in the form of paper, paper transparencies, a compact disk, a DVD, an integrated circuit, a hard disk, a floppy disk, an optical disk, a magnetic tape, a RAM, a ROM, a PROM, a EPROM, a wire, a cable, a fiber, communications channel, a satellite transmissions or other remote transmission, as well as any other medium or source of data that may be read by the processors of the invention.

Further, the memory or memories used in the processing machine that implements the invention may be in any of a wide variety of forms to allow the memory to hold instructions, data, or other information, as is desired. Thus, the memory might be in the form of a database to hold data. The database might use any desired arrangement of files such as a flat file arrangement or a relational database arrangement, for example.

In the system and method of the invention, a variety of "user interfaces" may be utilized to allow a user to interface with the processing machine or machines that are used to implement the invention. As used herein, a user interface includes any hardware, software, or combination of hardware and software used by the processing machine that allows a user to interact with the processing machine. A user interface may be in the form of a dialogue screen for example. A user interface may also include any of a mouse, touch screen, keyboard, voice reader, voice recognizer, dialogue screen, menu box, list, checkbox, toggle switch, a pushbutton or any other device that allows a user to receive information regarding the operation of the processing machine as it processes a set of instructions and/or provide the processing machine with information. Accordingly, the user interface is any device that provides communication between a user and a processing machine. The information provided by the user to the processing machine through the user interface may be in the form of a command, a selection of data, or some other input, for example.

As discussed above, a user interface is utilized by the processing machine that performs a set of instructions such that the processing machine processes data for a user. The user interface is typically used by the processing machine for interacting with a user either to convey information or receive information from the user. However, it should be appreciated that in accordance with some embodiments of the system and method of the invention, it is not necessary that a human user interact with a user interface used by the processing machine of the invention. Rather, it is also contemplated that the user interface of the invention might interact, i.e., convey and receive information, with another processing machine, rather than a human user. Accordingly, the other processing machine might be characterized as a user. Further, it is contemplated that a user interface utilized in the system and method of the invention may interact partially with another processing machine or processing machines, while also interacting partially with a human user.

What is claimed is:

1. A notification network providing improved efficiency of notification to a user, the network comprising:
   a plurality of devices associated with the user;
   an server processor, being part of a content aware notification delivery (CAND) system, the server processor including instructions on a non-transitory computer medium, the non-transitory computer medium constituted by one of more data storage mediums and the server processor processing the instructions;
   a database of known data about the user and the plurality of devices, the database resident on the non-transitory computer medium; and
   a notification system, being part of the CAND system, the notification system consisting of a notification manager, a delivery manager, and a communication portion, wherein the notification system sends notification communications to the user through one or more of the plurality of devices;
   wherein, the plurality of devices, server processor, database, and notification system are in communication to form the notification network which is configured to perform operations including:
      the server processor determining physical accessibility of the user by a first comparing of current data from the plurality of devices in the network against known data in the database relating to the user's physical accessibility, and the first comparing including determining if respective values of first current data, of the current data, when aggregated, with each respective value of the first current data being weighted, satisfies first window criteria;

the server processor mapping a plurality of cognitive data parameters from the database of known data about the user;

the server processor identifying a set of cognitive patterns from the mapping of the plurality of cognitive data parameters, wherein the set of cognitive patterns are indicative of the user being cognitively aware and ready to act on at least one notification;

the server processor determining a set of observed data from the plurality of devices matches at least one identified cognitive pattern from the mapping to create a second window criteria; and the server processor generating and sending instructions, constituted by generating instruction data and sending the instruction data in a signal, to the notification system for the notification manager to select a notification from a notification queue of prioritized notifications, the selected notification being selected based on the following conditions: (1) the server processor performs processing to determine the selected notification should be transmitted to the user; (2) the server processor performs processing to determine the user is physically accessible based on whether the first window criteria is satisfied; (3) the server processor performs processing to determine the user is cognitively accessible based on whether the second window criteria is satisfied; (4) the server processor performs processing to determine it is the right time to send the notification; and (5) the server processor performs processing to determine which is the best device to send the notification from plurality of devices; and the delivery manager transmitting the selected notification to the best device through the communication portion.

2. The notification network of claim 1, the plurality of devices including at least one computing device and at least one sensor.

3. The notification network of claim 2, wherein the plurality of devices includes a first sensor in the user's home, a second sensor in the user's office, and the user's computing device.

4. The notification network of claim 2, the at least one sensor constituting a position movement sensor.

5. The notification network of claim 1, the server processor determining physical accessibility of the user based on data associated with the user's use of one of the plurality of devices.

6. The notification network of claim 1, wherein the plurality of devices includes a companion computing device, the companion computing device associated with a companion from the group consisting of a family member, a caregiver, a friend, a co-worker, or a researcher associated with the user.

7. The notification network of claim 1, the server processor determining which of the plurality of devices to transmit the notification based on power data of a device associated with the user, said device being one of the plurality of devices associated with the user.

8. The notification network of claim 7, wherein the power data is a power level of a device.

9. The notification network of claim 7, wherein the power data is a power consumption profile of a device.

10. The notification network of claim 1, wherein the operations include the server processor determining which of the plurality of devices to transmit the notification based on network efficiency data.

11. The notification network of claim 10, wherein the network efficiency data is cost of bandwidth along a communication path to a device associated with the user, said device being one of the plurality of devices associated with the user.

12. The notification network of claim 10, wherein the network efficiency data is a communication path reliability to a device associated with the user, said device being one of the plurality of devices associated with the user.

13. The notification network of claim 1, the server processor determining which of the plurality of devices to transmit the notification based on a reliability of a communication path and a cost of bandwidth to a device associated with the user, said device being one of the plurality of devices associated with the user.

14. The notification network of claim 1, the instruction data to the notification system including identification on which of the plurality of devices should receive the notification.

15. A notification network providing improved efficiency of notification to a user, the network comprising:

a plurality of devices associated with the user;

an server processor, being part of a content aware notification delivery (CAND) system, the server processor including instructions on a non-transitory computer medium, the non-transitory computer medium constituted by one of more data storage mediums, and the server processor processing the instructions;

a database of known data about the user and the plurality of devices, the database resident on the non-transitory computer medium; and a notification system, being part of the CAND system and consisting of a notification manager, a delivery manager, and a communication portion, wherein the notification system that sends notification communications to the user through one or more of the plurality of devices;

the plurality of devices, server processor, database, and notification system are in communication to form the notification network which is configured to perform operations including:

the server processor determining physical accessibility of the user by a first comparing of current data from the plurality of devices in the network against known data in the database relating to the user's physical accessibility, and the first comparing including determining if respective values of first current data, of the current data, when aggregated, with each respective value of the first current data being weighted, satisfies first window criteria;

the server processor mapping a plurality of cognitive data parameters from the database of known data about the user;

the server processor identifying a set of cognitive patterns from the mapping of the plurality of cognitive data parameters, wherein the set of cognitive patterns are indicative of the user being cognitively aware and ready to act on at least one notification;

the server processor determining a set of observed data from the plurality of devices matches at least one identified cognitive pattern from the mapping to create a second window criteria; and the server processor generating and sending instructions, constituted by generating instruction data and sending the instruction data in a signal, to the notification system for the notification manager to select a notification from a notification queue of prioritized notification, and for the delivery manager and communication portion to send the selected notification to the user when the following conditions are met: (1) the server processor performs processing to determine the notification should be transmitted to the user; (2) the server processor performs processing to determine the user is physically accessible based on whether the first window criteria is satisfied; (3) the server processor performs processing to determine the user is cognitively accessible based on whether the second window criteria is satisfied; (4) the server processor performs processing to determine it is the right time to send the notification; and (5) the server processor performs processing to determine which is the best device to send the notification from plurality of devices the server processor determining physical accessibility of the user based on data associated with the user's use of one of the plurality of devices;

the plurality of devices including at least one computing device and a plurality of sensors;

the plurality of sensors includes a first sensor in the user's home, a second sensor in the user's office, and the user's computing device;

the server processor performs processing to determine which of the plurality of devices to transmit the notification based on power data of a device associated with the user, the device being one of the plurality of devices associated with the user;

the power data is one of a power level of the device or a power consumption profile of the device;

the server processor performs processing to determine which of the plurality of devices to transmit the notification based on network efficiency data;

the network efficiency data is one of a cost of bandwidth along a communication path to a device associated with the user, and the communication path reliability to a device associated with the user; and the instruction data to the notification system including identification on which of the plurality of devices should receive the notification.

* * * * *

UNITED STATES PATENT AND TRADEMARK OFFICE
CERTIFICATE OF CORRECTION

| | |
|---|---|
| PATENT NO. | : 10,756,957 B2 |
| APPLICATION NO. | : 15/804201 |
| DATED | : August 25, 2020 |
| INVENTOR(S) | : Praduman Jain and Josh Schilling |

Page 1 of 1

It is certified that error appears in the above-identified patent and that said Letters Patent is hereby corrected as shown below:

On the Title Page

Item (54) and in the Specification, In Column 1, Line 1, delete "CONTEXT BASED" and insert -- CONTEXT-BASED --, therefor.

In the Claims

In Claim 8, Column 43, Line 65, delete "a device." and insert -- the device. --, therefor.

In Claim 9, Column 43, Line 67, delete "a device." and insert -- the device. --, therefor.

Signed and Sealed this
Thirteenth Day of October, 2020

Andrei Iancu
*Director of the United States Patent and Trademark Office*